(12) United States Patent
Van Dyke

(10) Patent No.: US 7,892,573 B2
(45) Date of Patent: Feb. 22, 2011

(54) NERVE REGENERATION EMPLOYING KERATIN BIOMATERIALS

(75) Inventor: Mark E. Van Dyke, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 267 days.

(21) Appl. No.: 11/673,212

(22) Filed: Feb. 9, 2007

(65) Prior Publication Data

US 2007/0298070 A1 Dec. 27, 2007

Related U.S. Application Data

(60) Provisional application No. 60/772,245, filed on Feb. 10, 2006.

(51) Int. Cl.
- A61F 2/00 (2006.01)
- A61K 35/30 (2006.01)
- A61K 8/65 (2006.01)
- A61B 17/08 (2006.01)

(52) U.S. Cl. .................. 424/426; 424/570; 524/916; 606/152

(58) Field of Classification Search .................. None
See application file for complete search history.

(56) References Cited

U.S. PATENT DOCUMENTS

| | | | |
|---|---|---|---|
| 2,236,921 | A | 4/1941 | Schollkopf et al. |
| 2,413,983 | A | 1/1947 | Lustig et al. |
| 3,464,825 | A | 9/1969 | Anker |
| 3,642,498 | A | 2/1972 | Anker |
| 4,570,629 | A | 2/1986 | Widra |
| 4,662,884 | A | 5/1987 | Stensaas |
| 5,468,253 | A | 11/1995 | Bezwada et al. |
| 5,656,605 | A | 8/1997 | Hansson et al. |
| 5,932,552 | A | 8/1999 | Blanchard et al. |
| 5,948,432 | A | 9/1999 | Timmons et al. |
| 6,063,757 | A | 5/2000 | Urso |
| 6,090,117 | A | 7/2000 | Shimizu |
| 6,110,487 | A | 8/2000 | Timmons et al. |
| 6,124,265 | A | 9/2000 | Timmons et al. |
| 6,159,495 | A | 12/2000 | Timmons et al. |
| 6,159,496 | A | 12/2000 | Blanchard et al. |
| 6,270,793 | B1 | 8/2001 | Van Dyke et al. |
| 6,379,690 | B2 | 4/2002 | Blanchard et al. |
| 6,432,435 | B1 | 8/2002 | Timmons et al. |
| 6,436,129 | B1 | 8/2002 | Sharkey et al. |
| 6,461,628 | B1 | 10/2002 | Blanchard et al. |
| 6,461,629 | B1 | 10/2002 | Tranquillo et al. |
| 6,506,727 | B1 | 1/2003 | Hansson et al. |
| 6,544,548 | B1 | 4/2003 | Siller-Jackson et al. |
| 6,589,257 | B1 | 7/2003 | Shimizu |
| 6,676,675 | B2 | 1/2004 | Mallapragada et al. |
| 6,746,836 | B1 | 6/2004 | Widra |
| 6,890,531 | B1 | 5/2005 | Horie et al. |
| 7,439,012 | B2 | 10/2008 | Van Dyke |
| 2003/0228353 | A1 | 12/2003 | Cowsar |
| 2007/0166348 | A1 | 7/2007 | Van Dyke |
| 2009/0017001 | A1 | 1/2009 | Van Dyke |

FOREIGN PATENT DOCUMENTS

| | | |
|---|---|---|
| EP | 0 454 600 A1 | 4/1991 |
| WO | WO 2007/098053 | 8/2007 |

OTHER PUBLICATIONS

Hu et al. (J Med Coll PLA 17(1): 10-13, 2002).*
Qiu et al. Glia, 29: 166-1174, 2000.*
Alibardi J Morphol 261:345-363, 2004.*
Buchanan, Biochem J. 167: 489-491, 1977.*
International Search Report and Written Opinion, PCT/US07/03639, mailed Jul. 7, 2008.
Hodgkinson GN et al. The differential influence of colocalized and segregated dual protein signals on neurite outgrowth on surfaces. Biomaterials, Jun. 2007; 28(16): 2590-2602.
Hu Q-L and Piao Y-J. Peripheral nerve repair by conduits made of human hair keratin: an experimental study. J. Med. Coll. PLA. 2002; 17(1): 10-13.
Migneault I et al. Glutaraldehyde: behavior in aqueous solution, reaction with proteins, and application to enzyme crossing. BioTechniques. 2004; 37(5): 790-802.
Hu Q et al. Experimental study of repairing peripheral nerve damage with conduit made of human hair keratin. J First Mil Med Univ. 2002; 22(9): 784-787.
Hu L et al. Mechanism of rat sciatic nerve regeneration induced by human hair keratin. J South Med Univ. 2008; 28(7): 1136-1140.
Madison RD et al. Peripheral nerve regeneration with entubulation repair: comparison of biodegradeable nerve guides versus polyethylene tubes and the effects of a laminin-containing gel. Experimental Neurology. 1987; 95: 378-390.
Valentini RF et al. Collagen- and laminin-containing gels impede peripheral nerve regeneration through semipermeable nerve guidance channels. Experimental Neurology. 1987; 98: 350-356.
Apel PJ et al. Peripheral nerve regeneration using a keratin-based scaffold: long-term functional and histological outcomes in a mouse model. J Hand Surg. 2008; 33A: 1541-1547.
Sierpinski P. et al. The use of keratin biomaterials derived from human hair for the promotion of rapid regeneration of peripheral nerves. Biomaterials. 2008; 29: 118-128.
Hill P et al. Some properties of keratin biomaterials: kerateines. Biomaterials. 2010; 31: 585-593.
Rouse JG and Van Dyke ME. A review of keratin-based biomaterials for biomedical applications. Materials. 2010; 3: 999-1014.
Supplementary European Search Report, EP 07750473, mailed Feb. 2, 2010.

(Continued)

Primary Examiner—Daniel E Kolker
Assistant Examiner—Aditi Dutt
(74) Attorney, Agent, or Firm—Myers Bigel Sibley & Sajovec, P.A.

(57) ABSTRACT

A keratin hydrogel matrix serves as an effective acellular scaffold for axonal regeneration and facilitates functional nerve recovery.

29 Claims, 14 Drawing Sheets

OTHER PUBLICATIONS

U.S. Appl. No. 11/676,072, filed Feb. 16, 2007, Mark Van Dyke.
U.S. Appl. No. 11/549,748, filed Oct. 16, 2006, Mark Van Dyke.
U.S. Appl. No. 11/205,800, filed Aug. 17, 2005, Mark Van Dyke.
Bertelli JA, Taleb M, Mira JC, Ghizoni MF. The course of aberrant reinnervation following nerve repair with fresh or denatured muscle autografts. *J Peripher Nerv Syst.* Dec. 2005;10(4):359-368.
Brandt J, Nilsson A, Kanje M, Lundborg G, Dahlin LB. Acutely-dissociated Schwann cells used in tendon autografts for bridging nerve defects in rats: A new principle for tissue engineering in nerve reconstruction. *Scand J Plast Reconstr Surg Hand Surg.* 2005;39(6):321-325.
Lee SJ, Van Dyke ME. Tissue engineering scaffolds from self-assembled human hair keratins. *Polym Prep* 2005;46(1):112.
Belkas JS, Munro CA, Schoichet MS, Midha R. Peripheral nerve regeneration through a synthetic hydrogel nerve tube. *Restor Neurol Neurosci.* 2005;23(1)19-29.
Yang Y, Gu X, Tan R, Hu W, Wang X, Zhang P, and Zhang T. Fabrication and properties of a porous chitin/chitosan conduit for nerve regeneration. Exp neurol. 2000;161(2):571-84.
Schmidt CE, Leach JB. Neural tissue engineering: strategies for repair and regeneration. *Annu Rev Biomed Eng.* 2003;5:293-347.
Evans GR. Peripheral nerve injury: a review and approach to tissue engineered constructs. *Anat Rec.* 2001;263:396-404.
Rodriguez FJ, Verdu E, Ceballos D, Navarro X. Nerve guides seeded with autologous schwann cells improve nerve regeneration. *Exp Neurol.* 2000;161(2):571-84.
Mitsui S, Ohuchi A, Hotta M, Tsuboi R, Ogawa H. Genes for a range or growth factors and cyclin-dependent kinase inhibitors are expressed by isolated human hair follicles. *British J Dermatol.* 1997:137:693-698.
Walter MA, Kurouglu R, Caulfield JB, Vasconez LO, and Thompson JA. Enhanced peripheral nerve regeneration by acidic fibroblast growth factor. *Lymphokine Cytokine Res.* 1993;12(3):135-41.
Crewther WG et al., The Chemistry of Keratins. Anfinsen CB Jr et al., editors. Advances in Protein Chemistry 1965. Academic Press. New York:191-346.
Goddard et al., A Study on Keratin. *J. Biol. Chem.* 106:605-14 (1934).
Thompson et al., Studies on Reduced Wool. *Aust. J. Biol. Sci.* 15:757-68 (1962).
Yamauchi, The development of Keratin: Characteristics of Polymer Films. *Fragrance J.* 21(5):62-67 (1993). (English Translation of Entire Document).
O'Donnell IJ et al. Studies on Oxidized Wool IV. Fractionation of Proteins Extracted from Wool on DEAE-cellulose Using Buffers Containing 8M Urea (1961) *Aust J Biol Sci* 14:461-474.

* cited by examiner

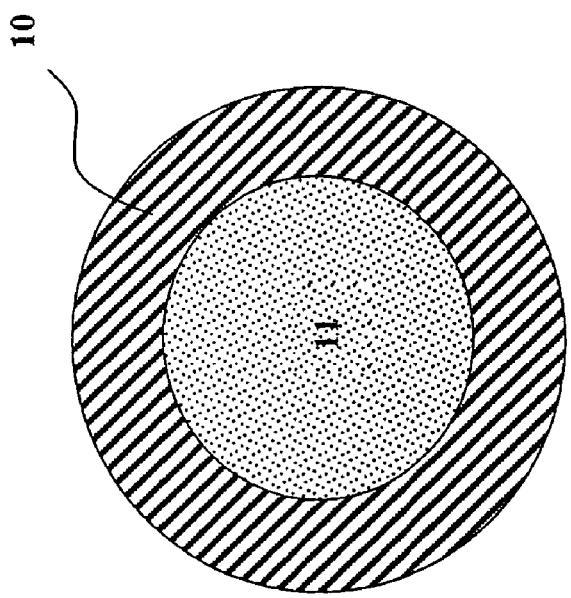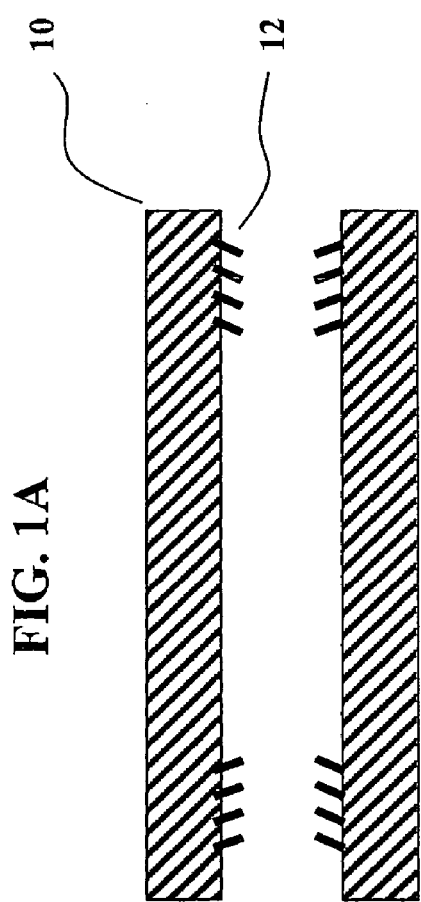
FIG. 1A
FIG. 1B

NERVE REGENERATION EMPLOYING KERATIN BIOMATERIALS

RELATED APPLICATIONS

This application claims the benefit under 35 U.S.C. §119 (e) of U.S. Provisional Patent Application Ser. No. 60/772, 245, filed Feb. 10, 2006, the disclosure of which is incorporated herein by reference in its entirety.

GOVERNMENT SUPPORT

This invention was made with government support under grants from the Department of Defense. The government has certain rights to this invention.

FIELD OF THE INVENTION

The present invention concerns methods and apparatus useful for facilitating the regeneration of damaged nerves.

BACKGROUND OF THE INVENTION

Nerve gaps/defects are common in various clinical situations, such as trauma and tumor ablation (Millesi H., *Surg Clin North Am.* 1981; 61:321-340; Millesi H., *Scand J Plast Reconstr Surg Suppl.* 1982; 19:25-37; Melendez M. et al., *Ann Plast Surg.* 2001; 46:375-381). Praemer et al. estimated that there are 18 million extremity injuries in the United States each year that result in a substantial number of peripheral nerve injuries (Praemer A. et al., Musculoskeletal conditions in the United States, 1999:3-162. Park Ridge, Ill. American Academy of Orthopaedic Surgeons). Over the past several decades, considerable research has been performed in an attempt to develop more effective techniques for the management of these injuries.

The current gold standard for nerve repair when a tension-free primary neurorrhaphy is not an option is the interpositional nerve autograft. The advent of nerve grafting in the early 1970s, along with the development of current microsurgical techniques, have greatly improved large nerve gap repair (Millesi H., *Orthop Clin North Am.* 1970; 2:419-435; Millesi H. et al., *J Bone Joint Surg (Am)*. 1972; 54:727-750; Millesi H. et al., *J Bone Joint Surg (Am)*. 1976; 58:209-218). However, grafting remains a technically demanding procedure associated with long operative times, donor site morbidity, and limited graft availability (Millesi H., *Clin Plast Surg.* 1984; 11:105-113; Millesi H., *Hand Clin.* 1986; 2:651-663; Millesi H., *Hand Clin.* 2000; 16:73-91, viii).

Peripheral nerve recovery following nerve injury and repair are impacted by numerous factors including level of injury, mechanism of disruption, patient age, tension at the repair site, type of repair, and time from injury to repair. Primary neurorrhaphy can be utilized for smaller nerve gaps, usually achieving good results if the anastamosis is performed tension free. Tension at the suture line is detrimental, encouraging connective tissue proliferation and the formation of scar (Dvali L. et al., *Clin Plast Surg.* 2003; 30:203-221). Sunderland described functional recovery following primary neurorrhaphy of nerve gaps up to 3-5 cm (Sunderland S., *Orthop Clin North Am.* 1981 April; 12(2):245-266). These repairs were made under slight tension and probably represented the upper limits of nerve gaps that are repairable using this approach. Primary nerve repairs eliminate the disadvantages associated with other techniques, thus, they remain one of the major reconstructive techniques used to manage defects.

For larger nerve defects that cannot be repaired in a tension-free fashion, several methods of interpositional nerve grafting are commonly used. Autogenous nerve grafting is often the first choice. Grafts are usually taken from thin cutaneous sensory nerves. These smaller nerves allow for more consistent revascularization of the graft. However, poor regeneration of motor nerves through sensory nerve grafts has been reported (Nichols C. et al., *Exp Neur,* 190(2004); 2:347-355).

For these reasons, much research has been focused on the development of effective alternatives to nerve grafting. Lundborg et al. showed increased regeneration rates using autogenous nerve pieces as a conduit filler in a rat model (Nilsson A. et al., *Scand J Plast Reconstr Surg Hand Surg.* 2005; 39(1):1-6). Trumble et al. successfully used an intact nerve bridge to repair a rat peroneal nerve gap (McCallister et al., *J of Reconstr Microsurg.* 2005; 3(21):197-206). Autogenous vein has also been studied as a biologic conduit, as has the use of skeletal muscle tissue and tendon as scaffolds (Mersa B. et al., *Kulak Burun Bogaz Ihtis Derg.* 2004; 13(5-6):103-11; Bertelli J. A. et al., *J Peripher Nerv Syst.* 2005 December; 10(4):359-68; Brandt J. et al., *Scand J Plast Reconstr Surg Hand Surg.* 2005; 39(6):321-5; Meek M. F. et al., *Tissue Eng.* 2004 July-August; 10(7-8):1027-36). Multiple other efforts have been made in biomaterials research and tissue engineering to develop and optimize nerve guidance channels and the scaffolds that fill them (Evans G. R. et al., *Anat Rec.* 2001; 263:396-404; Dvali L. et al., *Clin Plast Surg.* 2003; 30:203-221; Meek M. F. et al., *J Reconstr Microsurg.* 2002; 18:97-109; Schmidt C. E. et al., *Annu Rev Biomed Eng.* 2003; 5:293-347; Belkas J. S. et al., *Neuro Research.* 2004; 26:151-160; Bunting S. et al., *J Hand Surg* (Br). 2005; 30(3):242-247; Katayama U. et al., *Biomaterials.* 2006; 27(3):505-518).

The potential of nerve conduits to enhance peripheral nerve regeneration while avoiding many of the pitfalls encountered with nerve grafting has stimulated the interest of many researchers. The concept of nerve conduits was first described by Gluck in 1880, who used a glass tube to repair a severed nerve (Gluck T., *Arch Klin Chir.* 1880; 25:606). Nerve guidance conduits can help prevent the invasion of scar tissue while directing axonal sprouting, and the insertion of an optimized tissue engineering scaffold into the conduit can enhance nerve regeneration (Schmidt C. E. et al., *Annu Rev Biomed Eng.* 2003; 5:293-347). In the past few decades, multiple biologic and synthetic materials have been used as conduits in an attempt to optimize the microenvironment of the regenerating nerve. The ideal scaffold provides an architecture for regenerative cells, promotes cell attachment, growth and migration, and contributes growth factors to encourage the formation of functional tissue. Acellular scaffolds have become a viable source for tissue engineered conduit matrices. However, these scaffolds, while often containing residual growth factors, have the potential to retard cell infiltration due to their dense architecture.

The need for optimized scaffolds results from the historically poor functional recovery seen with empty nerve conduits used to repair large nerve defects (Belkas J. S. et al., *Neurol Res.* 2004; 26:151-160; Chen L. E. et al., *J Reconstr Microsurg.* 1994; 10:137-144; Chiu D. T. et al., *Plast Reconstr Surg.* 1990; 86:928-934; Chiu D. T., *Hand Clin.* 1999; 15:667-71, ix; Mosahebi A. et al., *Tissu Eng.* 2003; 9:209-218). Currently, the use of nerve conduits is limited to smaller diameter nerves with gaps of 3 cm or less (Dvali L. et al., *Clin Plast Surg.* 2003; 30:203-221). However, when conduits are used in conjunction with an optimized, tissue engineered scaffold nerve regeneration and functional recovery may be enhanced (Schmidt C. E. et al., *Annu Rev Biomed Eng.* 2003; 5:293-347).

The normal cascade of nerve injury and regeneration has been extensively reviewed (Göran Lundborg. *Nerve Injury and Repair,* 2nd Edition. Elsevier Inc., Philadelphia, Pa. (2004)). After nerve axotomy, the proximal segment degenerates at least to the nearest node of Ranvier. If a nerve guidance tube is used to repair the newly created gap, the conduit fills with fluid that contains neurotrophic factors and inflammatory cells. Within days, a well organized, longitudinal fibrin matrix forms that contains laminin and fibronectin. This provisional matrix is invaded by macrophages, Schwann cells, fibroblasts, and microvessels from both the proximal and distal nerve stumps. Axons begin to invade this matrix along with additional Schwann cells from the proximal side of the injury and within a few weeks, depending on the size of the gap, reach the distal side of the gap. Extensive remodeling occurs over the course of several months as the regenerating axons reach their targets and become myelinated.

Temporary support of early invading neuronal cells is a classic example of a neuroconductive material and is the mechanism by which most biomaterial fillers act. Neuroconductive biomaterials can support neuronal growth, but do not necessarily enhance cell function, a characteristic reserved for neuroinductive materials. As a consequence, regeneration across large gaps is difficult and highly dependent on the patient-related criteria mentioned earlier. To overcome this, investigators have implemented the use of autologous Schwann cells added to the biomaterial filler (Ansselin A. D. et al., Neuropathol Appl Neurobiol 1997; 23(5):387-98; Rodriguez F. J. et al., Exp Neurol 2000; 161(2):571-84; Strauch B. et al., J Reconstr Microsurg 2001; 17(8):589-95), as well as neurotrophic factors (Lee A. C. et al., Exp Neurol 2003; 184(1):295-303; Walter M. A. et al., Lymphokine Cytokine Res 1993; 12(3):135-41). Isolation of autologous Schwann cells still requires nerve tissue harvested from the patient, and in that sense differs little from autograft. Stem cells have been viewed as a solution to this dilemma and have been used in both differentiated and undifferentiated states (Tohill M. et al., Biotechnol Appl Biochem 2004; 40(1):17-24). While this approach has garnered much attention, particularly for application to the central nervous system, neuronal phenotypes are among the most difficulty to reliably differentiate in high yields from adult stem cells, the most likely source for near-term clinical application to peripheral nerve repair (Kokai L. E. et al., Plast Reconstr Surg 2005; 116(5):1453-60; Chen Y. et al., Cell Mol Life Sci 2006; 63(14):1649-57).

Therefore, there remains a need for optimal biomaterial fillers that promote both the regrowth and functional recovery of injured nerves.

SUMMARY OF THE INVENTION

A first aspect of the present invention is a device for promoting the growth of a nerve in a mammal, comprising:

a support structure having an elongate opening therein, such as a tubular encasing structure, configured for placement adjacent or around a damaged region of a nerve; and a physiologically acceptable matrix composition for placement in the elongate opening, through which or in which the nerve may grow. The matrix composition typically comprises a suitable amount (e.g., from 5 to 95 percent by weight) of keratin such as one or more keratin derivatives, e.g., alpha keratose, gamma keratose, kerateine, fractions thereof, and/or mixtures thereof, typically hydrated in a liquid (e.g., from 5 to 95 percent by weight) such as water (optionally containing physiologically acceptable salts), and the matrix may optionally contain other active ingredients such as one or more growth factors.

A further aspect of the present invention is the use of a matrix composition comprising keratin or a keratin material as described herein for the preparation of a device for carrying out a method as described herein.

Another aspect of the present invention is a kit comprising a support structure and a container, wherein, said support structure is packaged in said container in sterile form. The kit may also comprise a keratin matrix composition, in hydrated or dehydrated form (e.g., for subsequent hydration once opened for use), or the keratin matrix composition may be packaged separately.

BRIEF DESCRIPTION OF THE DRAWINGS

FIG. 1A. Cross section of a tubular support structure 10 defining an elongate opening 11 therein.

FIG. 1B. Longitudinal section of a tubular support structure 10 having fastening prongs 12 to facilitate securing the support structure onto the nerve.

DETAILED DESCRIPTION OF THE PREFERRED EMBODIMENTS

Figure 2:
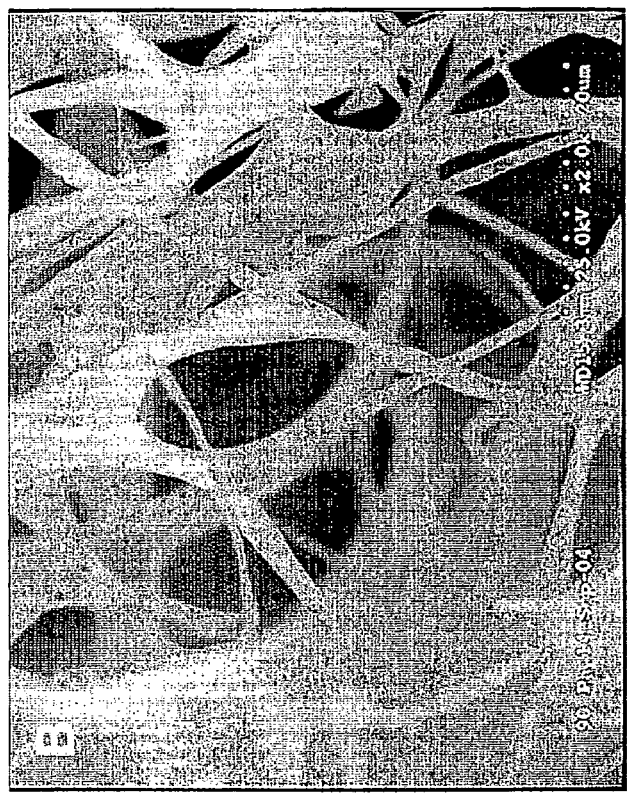
FIG. 2. Scanning electron microscopic images of two different keratin hydrogels at 300× (A) and 2000× (B). These architectures were formed by a process of self-assembly wherein the keratin proteins arrange themselves into a fibrous network.
Figure 2:
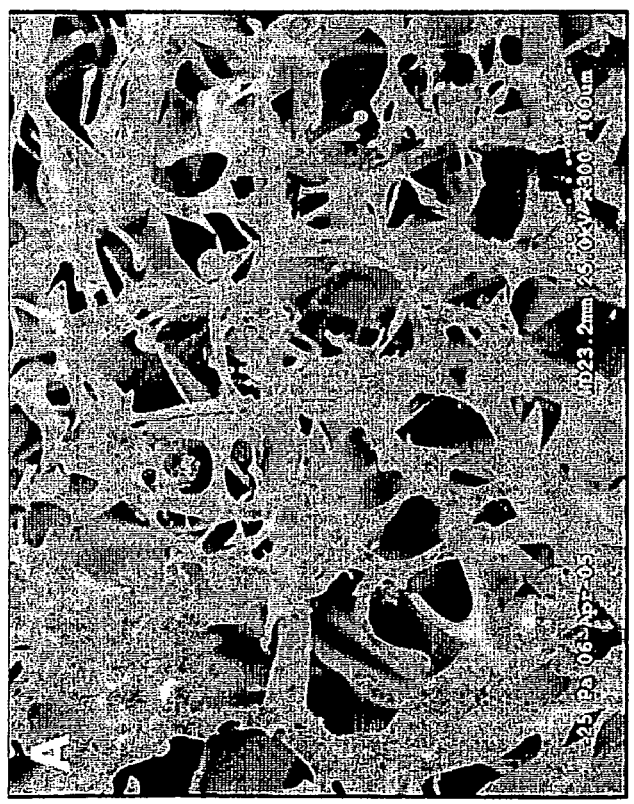

The disclosures of all United States patents cited herein are hereby incorporated by reference herein in their entirety.

Keratins extracted from hair are a novel group of biomaterials that may provide an alternative to other nerve conduit fillers. Porous keratin scaffolds in the form of a matrix promote cell binding, and contain multiple growth factors. In many instances the biocompatibility of keratin was found to exceed that of other naturally-derived biomaterials (Lee S. J. et al., Polym Prep 2005; 46(1):112). Also, certain keratin preparations have the ability to self-assemble into complex morphologies amenable to cell infiltration (Lee S. J. et al., Polym Prep 2005; 46(1):112). Keratose, an oxidized derivative of keratin, can self-assemble into nanofilaments when placed in solution. These nanofilaments then can further self-assemble into a fibrous micro-architecture on gelation. Important aspects of this self-assembly mechanism are: 1) it occurs spontaneously under benign conditions, and 2) it results in a homogeneous, porous morphology which facilitates the infiltration of regenerative cells. Cell binding to porous keratin scaffolds is facilitated by fibronectin-like binding domains (Tachibana A. et al., J Biotech 2002; 93: 165-7). Additionally, human hair has been identified as a depot of growth factors involved in normal follicle cycling, including nerve growth factor (Stenn K. S. et al., J Dermatology Sci 1994; 7S:S109-24).

One of the main purposes of using a biomaterial in tissue regeneration is to provide a surrogate extracellular matrix (ECM) for cells to attach and grow. Specific interactions to ECM binding sites through cell receptors are important in maintaining proper cell function (Ingber D., Curr Opin Cell Biol 1991; 3(5):841-8; Tooney P. A. et al., Immunol Cell Biol 1993; 71(2):131-9; Jockusch B. M. et al., Annu Rev Cell Dev Biol 1995; 11:379-416; Ruoslahti E., Annu Rev Cell Dev Biol 1996; 12:697-715). Cells attach to the ECM through more than 20 known integrin receptors, more than half of which bind to the Arginine-Glycine-Aspartic Acid (RGD) peptide motif (Ruoslahti E., Annu Rev Cell Dev Biol 1996; 12:697-715). An inspection of the more than 70 known human hair keratin protein sequences reveals that 78% contain at least one binding domain specific to the integrins expressed on many cell types, and 23% contain two or more such domains (Entrez Protein Database, National Center for Biotechnology Information (NCBI).

Through the use of biomaterials that are both neuroconductive and neuroinductive, regeneration across large nerve defects may be possible. Hair follicle morphogenesis is a highly regenerative process that is mediated by a host of regulatory and matrix molecules. Genes for several neurotrophic factors have been shown to be expressed in both human and animal hair follicle, including growth factors prominent in nerve regeneration such as insulin-like growth factor, nerve growth factor and fibroblast growth factor (Ishii D. N. et al., Pharmacol Ther 1994; 62(1-2):125-44; Fu S. Y. and Gordon T., Mol Neurobiol 1997; 14(1-2):67-116; Frostick S. P. et al., Microsurgery 1998; 18(7):397-405; Grothe C. and Nikkhah G. Anat Embryol (Berl) 2001; 204(3):171-7). The presence of some of the actual proteins has been confirmed by immunohistochemical techniques (Little J. C. et al., J Invest Dermatol 1994; 103(5):715-20; Mitsui S. et al., Br J Dermatol 1997; 137(5):693-8).

Subjects to be treated by the present invention include both human and animal subjects, particularly mammalian subjects such as dogs, cats, horses, cattle, mice, monkeys, baboons, etc., for both human and veterinary medicine purposes and drug and device development purposes.

Nerves to be treated by the methods of the invention include afferent, efferent and mixed peripheral nerves such as somatic nerves, sensory-somatic nerves (including the cranial and spinal nerves), and autonomic nerves, which include sympathetic nerves, and parasympathetic nerves. Examples of nerves to be treated include, but are not limited to, cranial nerves, spinal nerves, nerves of the brachial plexus, nerves of the lumbar plexus, musculocutaneous nerve, femoral nerve, obturator nerve, sciatic nerve, the intercostal nerves, subcostal nerve, ulnar nerve, radial nerve, median nerve, pudendal nerve, saphenous nerve, common peroneal nerve, deep peroneal nerve, superficial peroneal nerve, and tibial nerve.

Damaged regions of nerves to be treated by the invention include those that have been subjected to a traumatic injury, such as crushed regions and severed (including fully and partially severed) regions in a limb, as well as nerves damaged in the course of a surgical procedure, e.g., as necessary to achieve another surgical goal. Damaged regions also include nerve regions that have degenerated due to a degenerative nerve disorder or the like, creating a "bottleneck" for axonal activity that can be identified by techniques such as electromyography and treated by use of the methods and devices of the present invention.

Enhancing cell migration has important implications in many regenerative processes. Functional repair of tissues is often size limited, due primarily by the inability of regenerative cells to migrate over long distances. In the case of nerve regeneration, infiltrating Schwann cells are driven by chemotactic mechanisms to migrate into the damaged nerve's provisional matrix and initiate the repair process. Materials that have the ability to mediate this process can be tested using the modified Boyden method (Boyden S. J Exp Med 1962; 115: 543-66).

Keratin Preparations.

After extrusion through the skin, the hair fiber is formed into a highly stable and robust structural tissue that is relatively impervious to environmental insult. The hair fiber contains structural macromolecules, crosslinkers, plasticizers, and UV stabilizers, which serve to protect the regulatory molecules contained within it. The useful contents of the hair fiber can be retrieved using chemical methods that break down the constituent matrix proteins called keratins.

The matrix compositions may comprise a keratin, including alpha keratose, gamma keratose, kerateine, kerateine fractions, mixtures thereof, etc., typically hydrated with a physiologically acceptable aqueous medium such as sterile water, sterile saline solution, etc. In some embodiments the keratin of the matrix compositions comprises a mixture of alpha and gamma keratose. In some embodiments the alpha and/or gamma keratose is acidic alpha and/or gamma keratose. In some embodiments the alpha and/or gamma keratose is basic alpha and/or gamma keratose. General procedures for the preparation of useful keratins are set forth below.

A preferred method for the production of keratoses is by oxidation with hydrogen peroxide, peracetic acid, or performic acid. A most preferred oxidant is peracetic acid. Preferred concentrations range from 1 to 10 weight/volume percent (w/v %), the most preferred being approximately 2 w/v %. Those skilled in the art will recognize that slight modifications to the concentration can be made to effect varying degrees of oxidation, with concomitant alterations in reaction time, temperature, and liquid to solid ratio. It has also been discussed by Crewther et al. that performic acid offers the advantage of minimal peptide bond cleavage compared to peracetic acid. However, peractic acid offers the advantages of cost and availability. A preferred oxidation temperature is between 0 and 100 degrees Celsius (° C.). A most preferred oxidation temperature is 37° C. A preferred oxidation time is between 0.5 and 24 hours. A most preferred oxidation time is 12 hours. A preferred liquid to solid ratio is from 5 to 100:1. A most preferred ratio is 20:1. After oxidation, the hair is rinsed free of residual oxidant using a copious amount of distilled water.

The keratoses are extracted from the oxidized hair using an aqueous solution of a denaturing agent. Protein denaturants are well known in the art, but preferred solutions include urea, transition metal hydroxides (e.g. sodium and potassium hydroxide), ammonium hydroxide, and tris(hydroxymethyl) aminomethane (tris base). A preferred solution is Trizma® base (a brand of tris base) in the concentration range from 0.01 to 1M. A most preferred concentration is 0.1M. Those skilled in the art will recognize that slight modifications to the concentration can be made to effect varying degrees of extraction, with concomitant alterations in reaction time, temperature, and liquid to solid ratio. A preferred extraction temperature is between 0 and 100 degrees Celsius. A most preferred extraction temperature is 37° C. A preferred extraction time is between 0.5 and 24 hours. A most preferred extraction time is 3 hours. A preferred liquid to solid ratio is from 5 to 100:1. A most preferred ratio is 40:1. Additional yield can be achieved with subsequent extractions with dilute solutions of tris base or deionized (DI) water. After extraction, the residual solids are removed from solution by centrifugation and/or filtration.

The crude extract can be isolated by first neutralizing the solution to a pH between 7.0 and 7.4. A most preferred pH is 7.4. Residual denaturing agent is removed by dialysis against DI water. Concentration of the dialysis retentate is followed by lyophilization or spray drying, resulting in a dry powder mixture of both gamma- and alpha-keratose. Alternately, alpha-keratose is isolated from the extract solution by dropwise addition of acid until the pH of the solution reaches approximately 4.2. Preferred acids include sulfuric, hydrochloric, and acetic. A most preferred acid is concentrated hydrochloric acid. Precipitation of the alpha fraction begins at around pH 6.0 and continues until approximately 4.2. Fractional precipitation can be utilized to isolate different ranges of protein with different isoelectric properties. Solid alpha-keratose can be recovered by centrifugation or filtration.

The alpha-keratose can be further purified by re-dissolving the solids in a denaturing solution. The same denaturing solutions as those utilized for extraction can be used, however a preferred denaturing solution is tris base. Ethylene diamine tetraacetic acid (EDTA) can be added to complex and remove trace metals found in the hair. A preferred denaturing solution is 20 mM tris base with 20 mM EDTA or DI water with 20 mM EDTA. If the presence of trace metals is not detrimental to the intended application, the EDTA can be omitted. The alpha-keratose is re-precipitated from this solution by dropwise addition of hydrochloric acid to a final pH of approximately 4.2. Isolation of the solid is by centrifugation or filtration. This process can be repeated several times to further purify the alpha-keratose.

After removal of the alpha-keratose, the concentration of gamma-keratose from a typical extraction solution is approximately 1-2%. The gamma-keratose fraction can be isolated by addition to a water-miscible non-solvent. To effect precipitation, the gamma-keratose solution can be concentrated by evaporation of excess water. This solution can be concentrated to approximately 10-20% by removal of 90% of the water. This can be done using vacuum distillation or by falling film evaporation. After concentration, the gamma-keratose solution is added dropwise to an excess of cold non-solvent. Suitable non-solvents include ethanol, methanol, acetone, and the like. A most preferred non-solvent is ethanol. A most preferred method is to concentrate the gamma-keratose solution to approximately 10 w/v % protein and add it dropwise to an 8-fold excess of cold ethanol. The precipitated gamma-keratose can be isolated by centrifugation or filtration and dried. Suitable methods for drying include freeze drying (lyophilization), air drying, vacuum drying, or spray drying. A most preferred method is freeze drying.

A preferred method for the production of kerateines is by reduction of the hair with thioglycolic acid or beta-mercaptoethanol. A most preferred reductant is thioglycolic acid (TGA). Preferred concentrations range from 1 to 10M, the most preferred being approximately 1.0M. Those skilled in the art will recognize that slight modifications to the concentration can be made to effect varying degrees of reduction, with concomitant alterations in pH, reaction time, temperature, and liquid to solid ratio. A preferred pH is between 9 and 11. A most preferred pH is 10.2. The pH of the reduction solution is altered by addition of base. Preferred bases include transition metal hydroxides, sodium hydroxide, and ammonium hydroxide. A most preferred base is sodium hydroxide. The pH adjustment is effected by dropwise addition of a saturated solution of sodium hydroxide in water to the reductant solution. A preferred reduction temperature is between 0 and 100° C. A most preferred reduction temperature is 37° C. A preferred reduction time is between 0.5 and 24 hours. A most preferred reduction time is 12 hours. A preferred liquid to solid ratio is from 5 to 100:1. A most preferred ratio is 20:1. Unlike the previously described oxidation reaction, reduction is carried out at basic pH. That being the case, keratins are highly soluble in the reduction media and are expected to be extracted. The reduction solution is therefore combined with the subsequent extraction solutions and processed accordingly.

Reduced keratins are not as hydrophilic as their oxidized counterparts. As such, reduced hair fibers will not swell and split open as will oxidized hair, resulting in relatively lower yields. Another factor affecting the kinetics of the reduction/ extraction process is the relative solubility of kerateines. The relative solubility rankings in water is gamma-keratose>alpha-keratose>gamma-kerateine>alpha-kerateine from most to least soluble. Consequently, extraction yields from reduced hair fibers are not as high. This being the case, subsequent extractions are conducted with additional reductant plus denaturing agent solutions. Preferred solutions for subsequent extractions include TGA plus urea, TGA plus tris base, or TGA plus sodium hydroxide. After extraction, crude fractions of alpha- and gamma-kerateine can be isolated using the procedures described for keratoses. However, precipitates of gamma- and alpha-kerateine re-form their cystine crosslinks upon exposure to oxygen. Precipitates must therefore be re-dissolved quickly to avoid insolubility during the purification stages, or precipitated in the absence of oxygen.

Residual reductant and denaturing agents can be removed from solution by dialysis. Typical dialysis conditions are 1 to 2% solution of kerateines dialyzed against DI water for 24 to 72 hours. Those skilled in the art will recognize that other methods exist for the removal of low molecular weight contaminants in addition to dialysis (e.g. microfiltration, chromatography, and the like). The use of tris base is only required for initial solubilization of the kerateines. Once dissolved, the kerateines are stable in solution without the denaturing agent. Therefore, the denaturing agent can be removed without the resultant precipitation of kerateines, so long as the pH remains at or above neutrality. The final concentration of kerateines in these purified solutions can be adjusted by the addition/removal of water.

Regardless of the form of the keratin (i.e. keratoses or kerateines), several different approaches to further purification can be employed to keratin solutions. Care must be taken, however, to choose techniques that lend themselves to keratin's unique solubility characteristics. One of the most simple separation technologies is isoelectric precipitation. In this method, proteins of differing isoelectric point can be isolated by adjusting the pH of the solution and removing the precipitated material. In the case of keratins, both gamma- and alpha-forms are soluble at pH>6.0. As the pH falls below 6, however, alpha-keratins begin to precipitate. Keratin fractions can be isolated by stopping the precipitation at a given pH and separating the precipitate by centrifugation and/or filtration. At a pH of approximately 4.2, essentially all of the alpha-keratin will have been precipitated. These separate fractions can be re-dissolved in water at neutral pH, dialyzed, concentrated, and reduced to powders by lyophilization or spray drying. However, kerateine fractions must be stored in the absence of oxygen or in dilute solution to avoid crosslinking.

Another general method for separating keratins is by chromatography. Several types of chromatography can be employed to fractionate keratin solutions including size exclusion or gel filtration chromatography, affinity chromatography, isoelectric focusing, gel electrophoresis, ion exchange chromatography, and immunoaffinity chromatography. These techniques are well known in the art and are capable of separating compounds, including proteins, by the characteristics of molecular weight, chemical functionality, isoelectric point, charge, or interactions with specific antibodies, and can be used alone or in any combination to effect high degrees of separation and resulting purity.

A preferred purification method is ion exchange (IEx) chromatography. IEx chromatography is particularly suited to protein separation owning to the amphiphilic nature of proteins in general and keratins in particular. Depending on the starting pH of the solution, and the desired fraction slated for retention, either cationic or anionic IEx (CIEx or AIEx, respectively) techniques can be used. For example, at a pH of 6 and above, both gamma- and alpha-keratins are soluble and above their isoelectric points. As such, they are anionic and can be bound to an anionic exchange resin. However, it has been discovered that a sub-fraction of keratins does not bind to a weakly anionic exchange resin and instead passes through a column packed with such resin. A preferred solution for AIEx chromatography is pure keratin, isolated as described previously, in purified water at a concentration between 0 and 5 weight/volume %. A preferred concentration is between 0 and 4 w/v %. A most preferred concentration is approximately 2 w/v %. It is preferred to keep the ionic strength of said solution initially quite low to facilitate binding to the AIEx column. This is achieved by using a minimal amount of acid to titrate a purified water solution of the keratin to between pH 6 and 7. A most preferred pH is 6. This solution can be loaded onto an AIEx column such as DEAE-Sepharose® resin or Q-Sepharose® resin columns. A preferred column resin is DEAE-Sepharose® resin. The solution that passes through the column can be collected and further processed as described previously to isolate a fraction of acidic keratin powder.

In some embodiments the activity of the keratin matrix is enhanced by using an AIEx column to produce the keratin to thereby promote cell adhesion. Without wishing to be bound to any particular theory, it is envisioned that the fraction that passes through an anionic column, i.e. acidic keratin, promotes cell adhesion. In addition, nerve growth factor (NGF), thought to be present in hair extracts, has an isoelectric point of 9.5-10. That being the case, NGF would also flow through the column under the stated conditions. The resulting acidic fraction provides an optimized matrix for nerve regeneration because it is capable of stimulating cell attachment in general, and nerve growth in particular.

Another fraction binds readily, and can be washed off the column using salting techniques known in the art. A preferred elution medium is sodium chloride solution. A preferred concentration of sodium chloride is between 0.1 and 2M. A most preferred concentration is 2M. The pH of the solution is preferred to be between 6 and 12. A most preferred pH is 12. In order to maintain stable pH during the elution process, a buffer salt can be added. A preferred buffer salt is Trizma® base. Those skilled in the art will recognize that slight modifications to the salt concentration and pH can be made to affect the elution of keratin fractions with differing properties. It is also possible to use different salt concentrations and pH's in sequence, or employ the use of salt and/or pH gradients to produce different fractions. Regardless of the approach taken, however, the column eluent can be collected and further processed as described previously to isolate fractions of basic keratin powders.

A complimentary procedure is also feasible using CIEx techniques. Namely, the keratin solution can be added to a cation exchange resin such as SP Sepharose® resin (strongly cationic) or CM Sepharose® resin (weakly cationic), and the basic fraction collected with the pass through. The retained acid keratin fraction can be isolated by salting as previously described.

The formation of a matrix comprising keratin materials such as described above can be carried out in accordance with techniques long established in the field or variations thereof that will be apparent to those skilled in the art. In some embodiments, the keratin preparation is dried and rehydrated prior to use. See, e.g., U.S. Pat. No. 2,413,983 to Lustig et al., U.S. Pat. No. 2,236,921 to Schollkipf et al., and U.S. Pat. No. 3,464,825 to Anker. In preferred embodiments, the matrix, or hydrogel, is formed by re-hydration of the lyophilized material with a suitable solvent, such as water or phosphate buffered saline (PBS). The gel can be sterilized, e.g., by γ-irradiation (800 krad) using a Co60 source. Other suitable methods of forming keratin matrices include, but are not limited to, those found in U.S. Pat. Nos. 6,270,793 (Van Dyke et al.), 6,274,155 (Van Dyke et al.), 6,316,598 (Van Dyke et al.), 6,461,628 (Blanchard et al.), 6,544,548 (Siller-Jackson et al.), and 7,01987 (Van Dyke).

The matrix may optionally contain one or more active ingredients such as one or more growth factors (e.g., in an amount ranging from 0.0000001 to 1 or 5 percent by weight of the matrix composition) to facilitate nerve growth. Examples of suitable active ingredients include, but are not limited to, nerve growth factor, vascular endothelial growth factor, fibronectin, fibrin, laminin, acidic and basic fibroblast growth factors, testosterone, ganglioside GM-1, catalase, insulin-like growth factor-I (IGF-I), platelet-derived growth factor (PDGF), neuronal growth factor galectin-1, and combinations thereof. See, e.g., U.S. Pat. No. 6,506,727 to Hansson et al. and U.S. Pat. No. 6,890,531 to Horie et al.

As used herein, "growth factors" include molecules that promote the regeneration, growth and survival of nervous tissue. Growth factors that are used in some embodiments of the present invention may be those naturally found in keratin extracts, or may be in the form of an additive, added to the keratin extracts or formed keratin matrices. Examples of growth factors include, but are not limited to, nerve growth factor (NGF) and other neurotrophins, platelet-derived growth factor (PDGF), erythropoietin (EPO), thrombopoietin (TPO), myostatin (GDF-8), growth differentiation factor-9 (GDF9), basic fibroblast growth factor (bFGF or FGF2), epidermal growth factor (EGF), hepatocyte growth factor (HGF), granulocyte-colony stimulating factor (G-CSF), and granulocyte-macrophage colony stimulating factor (GM-CSF). There are many structurally and evolutionarily related proteins that make up large families of growth factors, and there are numerous growth factor families, e.g., the neurotrophins (NGF, BDNF, and NT3). The neurotrophins are a family of molecules that promote the growth and survival of nervous tissue. Examples of neurotrophins include, but are not limited to, nerve growth factor (NGF), brain-derived neurotrophic factor (BDNF), neurotrophin 3 (NT-3), and neurotrophin 4 (NT-4). See U.S. Pat. Nos. 5,843,914 to Johnson, Jr. et al.; 5,488,099 to Persson et al.; 5,438,121 to Barde et al.; 5,235,043 to Collins et al.; and 6,005,081 to Burton et al.

For example, nerve growth factor (NGF) can be added to the keratin matrix composition in an amount effective to promote the regeneration, growth and survival of nervous tissue. The NGF is provided in concentrations ranging from 0.1 ng/mL to 1000 ng/mL. More preferably, NGF is provided in concentrations ranging from 1 ng/mL to 100 ng/mL, and most preferably 10 ng/mL to 100 ng/mL. See U.S. Pat. No. 6,063,757 to Urso.

Devices and Methods of Use.

As used herein, "support structure," "conduit," "scaffold," etc., is any suitable structure into which a damaged nerve may be placed, and can support or contain the keratin matrix material during nerve regeneration. In general, the structure is formed of a physiologically acceptable material. As shown in FIGS. 1A and 1B, in some embodiments the support structure 10 has an elongate opening 11 formed therein. While FIGS. 1A and 1B show a conduit structure in the shape of a tube having a single longitudinal opening, any suitable shape, including square, hexagonal, triangular, etc., with any number of openings (such as fibrils as described below) may be used. Other examples of embodiments suitable to carry out the present invention will be apparent to those skilled in the art. For example, the support structure can be in the shape of a gutter, with or without an additional top piece. The gutter support structure may also have a top piece, placed in such a way as to "sandwich" the damaged nerve between the two pieces.

The material from which the support structure is formed can be bioabsorbable or inert (that is, non-bioabsorbable). Any bioabsorbable material may be used, including but not limited to natural materials such as collagen, laminin, alginate and combinations thereof, etc., as well as synthetic materials such as poly(lactide), poly(glycolide), poly(caproic acid), combinations thereof, etc. Materials may be polymeric or non-polymeric. Examples of suitable support structures include, but are not limited to, the artificial neural tubes described in U.S. Pat. Nos. 6,589,257 and 6,090,117 to Shimizu, the guide tubes described in U.S. Pat. No. 5,656,605 to Hansson et al., the tubular prostheses described in U.S. Pat. No. 4,662,884 to Stensaas, the elastomeric devices described in U.S. Pat. No. 5,468,253 to Bezwada et al., and the biopolymer rods with oriented fibrils (which fibrils then form a plurality of elongate openings or tubes containing the matrix described herein) as described in U.S. Pat. No. 6,461,629 to Tranquillo et al.

Other options for configuration of the support structure include having a longitudinal slit to facilitate the positioning of the structure around a damaged nerve, such as described in U.S. Pat. No. 4,662,884 to Stensaas. The interior wall portion of the support structure may optionally be patterned to facilitate or guide regeneration, as described in U.S. Pat. No. 6,676,675 to Mallapragada et al. The elongate opening may optionally contain guiding filaments dispersed within the matrix and extending along the logitudinal dimension of the support structure, as described in U.S. Pat. No. 5,656,605 to Hansson et al. The support structure may optionally include one, two or more electrodes connected to or otherwise operatively associated therewith to aid in applying an electric field to the nerve to facilitate regeneration.

The support structure may be packaged in sterile form in a sterile aseptic container. The sterile matrix composition may be provided in the support structure as packaged, in hydrated or dehydrated form (for subsequent hydration with a suitable solution such as sterile physiologically acceptable saline solution once opened for use), or the matrix packaged separately (in hydrated or dehydrated form, in a vial, syringe, or any other suitable container) for administration into the support structure before or during the time of use.

In some embodiments, the support structure is positioned around the damaged region of the nerve, and matrix is added as necessary. This may be carried out by any suitable technique, such as by opening the structure (e.g., along a longitudinal slit) and then enclosing it around the damaged portion of the nerve, by inserting each stump (proximal, distal) of a severed nerve into opposite ends of the support structure opening, etc. Sutures, surgical adhesives, staples, clasps, prongs formed on the inner surface of the support structure at each end thereof, or any other suitable technique may be used to secure the nerve in place. FIG. 1B shows a support structure embodiment having one or more fastening prongs 12 on the inner wall thereof at both end portions thereof to facilitate securing the structure onto the nerves, which prongs can be in any suitable shape (e.g., dimples, whiskers, pointed, blunt, etc.) formed by any suitable technique such as molding, microstamping, printing, lithography, crimping or partially punching, etc., depending upon the particular material from which the support structure is formed.

Surgical procedures can otherwise be carried out in accordance with known techniques, including but not limited to those described in U.S. Pat. Nos. 6,589,257 and 6,090,117 to Shimizu, U.S. Pat. No. 5,656,605 to Hansson et al., U.S. Pat. No. 4,662,884 to Stensaas, U.S. Pat. No. 5,468,253 to Bezwada et al., and U.S. Pat. No. 6,676,675 to Mallapragada et al.

The present invention is explained in greater detail in the following non-limiting examples.

Example 1

Keratin Preparation

Keratins were extracted from human hair. 25 g of clean dry hair was oxidized with a 2 w/v % solution of peracetic solution at a liquid:solid ratio of 40:1. The oxidation was carried out at 37° C. with constant gentle stirring for 12 hours. After oxidation, the hair was recovered by sieve and rinsed with copious amounts of deionized (DI) water. The oxidized hair was extracted with 1 L of 100 mM tris base at 37° C. with gentle stirring for 12 hours. The hair was recovered by sieve and extracted again with 1 L of DI water at 37° C. with gentle stirring for 12 hours. Concurrently, the tris base solution was neutralized to pH 7.4 by dropwise addition of hydrochloric acid and refrigerated. The hair from the DI water extraction was separated by sieve and discarded. The liquid was recovered, neutralized to pH 7.4, and combined with the first extract. The extract solution was then centrifuged, filtered, and dialyzed against DI water with a dialysis cartridge having a 1,000 Dalton nominal low molecular weight cutoff for 24 hours. After dialysis, the keratose solution was concentrated, neutralized to pH 7.4, frozen at −80° C., and freeze dried. The resulting solid keratose was ground into a powder before use. To prepare the conduits, the powder was re-hydrated with phosphate buffered saline at a solids content between 15 and 20 wt. %.

Example 2

Animal Model

The ability of keratin to accelerate nerve regeneration, enhance functional recovery, and increase gap bridging capabilities was evaluated. This was accomplished by comparing the functional recovery (electrophysiology and muscle force generation) and structure (histologically) of a transected peripheral nerve repaired with an empty nerve conduit with a peripheral nerve repaired with a conduit filled with a keratin hydrogel matrix.

Eleven adult male Swiss Webster mice (20 g) were used in this study. Each animal was randomly placed into Group 1 (n=6) empty nerve conduit or Group 2 (n=5) keratin filled nerve conduit. The nerves from all animals were harvested at 6 weeks.

Before surgery, each animal was anesthetized with isoflurane (1-1.5 vol %), and the operative site was shaved and cleansed with Betadine® antiseptic. All surgical procedures were performed using aseptic technique. A 1.5 cm incision was made on the dorsum of the left thigh and the sciatic nerve was identified by dissection through the fascial plane separating the vastus lateralis and biceps femoris muscles. The tibial nerve was then separated from the common peroneal and sural nerves proximally, from its insertion into the gastrocnemius muscle to the tendon of obturator externus. The tibial nerve was then transected 5 mm proximal to its insertion into the gastrocnemius. The proximal and distal nerve ends were secured inside a 7 mm nerve conduit made of Silastic® polymer laboratory tubing (0.64±0.13 mm inside diameter, 1.19±0.13 mm outside diameter, 0.28 mm wall diameter, Dow Corning, Mich., USA) using 10-0 microsuture. The nerve gap within the conduit, defined as the distance between the proximal and distal nerve ends, was measured at 4.0 mm in all animals. The contralateral limb of each animal served as a control. A deep muscle closure was then performed around the conduit using 8-0 microsuture, followed by superficial muscle and skin closure with 5-0 Vicryl® suture. The wound was then coated with Neosporin® triple antibacterial ointment.

Example 3

Placement of Nerve Conduit & Tissue Engineering Matrix

Fixation of the nerve conduit began with the introduction of the suture needle into the conduit lumen 1.5 mm from the distal end. The suture was then threaded through the lumen until approximately 4 mm of the suture tail remained outside of the conduit wall. The suture needle was then placed into the end of the distal nerve segment and, while running parallel to the axon fibers, driven 1 mm into and out of the nerve, securing the epineurium and perineurium. Rotating the nerve fiber 120°, the suture needle was reintroduced into the distal nerve and while running parallel to the axon fibers, driven 1 mm back through the perineurium and out the distal nerve end. The needle was then reintroduced into the lumen of the nerve conduit, exiting the conduit wall 1.5 mm from the distal end, near the suture tail. The distal nerve end was then pulled 1.5 mm into the conduit by the suture ends, and the suture was tied with a surgeon's knot.

The conduit/nerve complex was then rotated 180° and an anchor suture was placed through the distal 0.25 mm of the conduit and into the epineurium before being secured with a surgeon's knot. The same procedure was followed in securing the proximal nerve stump into the proximal end of the conduit.

A final "box" type suture was then placed to provide added security against nerve end "pull out" because the animals were allowed to roam freely within their cages post-operatively. This suture was placed by driving the suture needle perpendicular to the conduit through the nerve and both conduit walls. This procedure was then repeated through the opposite end of the conduit and secured with a surgeon's knot.

In Group 1, the procedure was concluded with the placement of the conduit. In Group 2, following placement of the proximal and distal nerve ends, a presterilized keratin gel was introduced into the 4 mm nerve gap using a 10 cc syringe and subcutaneous needle. The needle was passed into the nerve gap by placing it between the internal wall of the conduit and the nerve end. The needle was then advanced to the distal end of the gap, and the keratin hydrogel was injected as the needle was withdrawn.

Example 4

Functional Testing (Electrophysiology and Muscle Force Generation)

Six weeks following the placement of the nerve conduit, each animal underwent functional testing of the tibial nerve. Following exposure of the tibial nerve, a Nicolet Viking IIe electrodiagnostic system (Nicolet Instrument Corp. Madison, Wis.) was used to test nerve latency and action potential amplitude. A bipolar stimulating electrode was placed on the tibial nerve at the level of the obturator externus tendon. The active recording electrode was placed on the gastrocnemius muscle belly with the reference recording electrode placed on the foot. The nerve was then stimulated with a constant current stimulus at a level of 1.0 milli-Amps for a duration of 0.1 milliseconds. The testing protocol was repeated three times; the latency and amplitude of the motor action potentials were averaged and expressed as a percentage of the control. The contralateral limb served as the control (Ma J., et al. *Am J Phys Med Rehabil.* 83(2004); 10:774-780).

Each limb was then immobilized using K-wires driven through the femur and the tibia to fix the leg to a wooden table, preventing motion of the limb during testing. The gastrocnemius remained in situ until the force generation studies were started. The plantaris and soleus tendons were transected, leaving the Achilles tendon/gastrocnemius complex isolated. A wire suture was tied around the distal end of the Achilles tendon. The tendon was then transected distal to the suture, and the suture was attached to a force transducer (Model FT03 Grass, Quincy, Mass.) connected to a force transducer amplifier (Model 13-G4615-50, Gould, Cleveland, Ohio). The tibial nerve was then directly stimulated 4 mm proximal to the conduit (Grass SD9 stimulator, Quincy, Mass.) with increasing voltage until the maximum isometric single twitch force was obtained. The frequency of stimulation was then increased until maximum tetanic contractile force was generated. The same procedure was repeated on the contralateral limb which served as the control (Ma J. et al., *Am J Phys Med Rehabil.* 83(2004); 10:774-780). Responses were recorded using a calibrated recording oscillograph (RS 3800, Cleveland, Ohio) connected to the force transducer. The single twitch force and maximum tetanic contractile force were expressed as a percentage of the measurement of the control side.

The latency (conduction delay) and amplitude of the motor action potential were calculated as a percentage of the control and were averaged in both groups. At 6 weeks, three animals showed no visible fiber regeneration in Group 1 and thus were assigned a latency value of 100% (conduction delay) and an amplitude recovery of 0. This assignment was repeated for one animal in Group 2 that had no visible regeneration.

After 6 weeks of tibial nerve regeneration, the latency revealed a significant difference (p=0.0417) in conduction delay between Group 1 (86.7%, SD=51.8) and Group 2 (32.8%, SD=38.3). The difference in recovery of amplitude of the motor action potential was also statistically significant (p=0.0419) between Group 1 (9%, SD=13.7) and Group 2 (27.8%, SD=16.7).

Muscle force generation was not performed on animals that displayed no visible nerve fiber regeneration at 6 weeks. In Group 1, the gastrocnemius generated a maximum single twitch force of 14 g and a maximum tetanus of 16 g. In Group 2, the gastrocnemius generated a maximum single twitch force of 16 g and a maximum tetanus of 56 g. Cross-sectional histology demonstrated regenerating myelinated axon fibers in both groups, with increased neovascularization in Group 2.

Example 5

Nerve Harvest

Following testing of the gastrocnemius muscle, the tibial nerve was transected 4 mm proximal and 4 mm distal to the nerve conduit. This nerve segment was then pinned to hardened silicone to prevent shrinkage. The nerves were covered in 4% paraformaldehyde for 24-48 hours, and then washed with a 0.15 mol/L phosphate buffer solution overnight. The nerve segments were then placed in a phosphate buffered saline, dehydrated in increasing concentrations of ethanol (70% to 100%), transferred to propylene oxide, and embedded in Epon® resin. Semi-thin sections (1 μm) cut from each pretrimmed block of tissue were then stained with toluidine blue and mounted on slides for analysis.

Data analysis was performed using Welch's correction of student's unpaired t test. Statistical significance was set at $p \leq 0.05$. At 6 weeks, only 50% (3/6) of the animals in Group 1 showed visible axon regeneration at 40× magnification across the 4 mm nerve gap whereas 80% (4/5) of the animals in Group 2 displayed visible fiber regeneration.

Example 6

Keratin Preparation

Human hair was obtained from a local barber shop, cut into small fibers, washed and degreased. Hair fibers were treated with a 2 wt/vol % solution of peracetic acid in DI water for 12 hours to oxidize the disulfide bonds to sulfonic acid. A 20 fold excess of this solution was used to oxidize the hair. All extractions were carried out on a reciprocating platform shaker (Barnstead/Lab-line Max Q 4000, Artisian Scientific, Champaign, Ill.) at 37° C., 180 rpm. After 12 hours, the hair was removed from the liquid by passing the solution through a 500 μm sieve (W.S. Tyler, Mentor, Ohio). Residual oxidant was removed by rinsing the hair with DI water for 5 minutes. Free proteins were extracted by placing the hair in a 40 fold excess of 100 mM tris base and shaking at 37° C. for one hour. A second extraction was performed by placing the hair in a 40 fold excess of DI water for one hour. Both extracts were retained by passage through a 500 μm sieve, neutralized, centrifuged (Sorvall Evolution RC, Thermo Electron, Asheville, N.C.) and filtered. The resulting extracts were purified for 24 hours by dialysis, concentrated and isolated by lyophilization (Freeze-Dry Systems, Labconco, Kansas City, Mo.).

Example 7

Structural Analysis of Keratin Biomaterial Hydrogel

The microstructure and architecture of the biomaterial hydrogels was investigated by scanning electron microscopy (SEM). Lyophilized hydrogels formed fibrous networks upon condensation. Morphologies ranged from ribbon-like to highly fibrous. Fiber diameters were on the order of 2-20 microns and pore sizes ranged from 20-50 microns. Interconnectivity of the pores—an important consideration for cellular infiltration during tissue regeneration through the hydrogel—was evident from cross sectional micrographs (FIG. 2).

A keratin hydrogel was formed by re-hydration of the lyophilized material with phosphate buffered saline (PBS) at a 15 wt/vol % concentration. The gel was sterilized by γ-irradiation (800 krad) using a Co60 source. The micro-architecture of the keratin hydrogel was examined by scanning electron microscopy (SEM). A 15% keratin hydrogel was lyophilized, fractured with a razor blade, mounted on stubs with colloidal graphite and examined using a variable pressure instrument (Model S-2600N, Hitachi High Technologies America, Inc., Pleasanton, Calif.). Hydrogels produced from keratin biomaterial possess a fibrous architecture with interconnected pores. This structure is important for the infiltration of regenerative cells from the proximal and distal nerve stumps and invasion of supportive vasculature as new tissue forms.

Example 8

In Vitro Cell Viability, Proliferation, Migration and Adhesion

Based on the premise that this keratin biomaterial contains minute amounts of regulatory molecules and larger amounts of matrix proteins, the biological activity on cellular function was tested by investigating the migration and proliferation of Schwann cells in the presence of keratin solutions, as well as the attachment of these cells to a keratin substrate. Moreover, it was investigated whether the keratin could serve as a provisional matrix, and that these neuroinductive characteristics would mediate improved functional recovery compared to autograft in an animal model of peripheral nerve injury.

A rat Schwann cell line, RT4-D6P2T, was obtained from the American Type Culture Collection (ATCC, Manassas, Va.) and used for all in vitro assays. Cells were cultured in Dulbecco's modified Eagle's medium (DMEM) high glucose media (Invitrogen®, Carlsbad, Calif.), supplemented with 10% fetal bovine serum (FBS, Cambrex Corp., East Rutherford, N.J.), 1% L-Glutamine and 1% penicillin-streptomycin. Cells were trypsinized prior to all experiments (Sigma-Aldrich, St. Louis, Mo.) and seeded accordingly for each assay. Cultures were grown at 37° C. in a humidified atmosphere supplemented with 5% CO2 in air.

Figure 3:
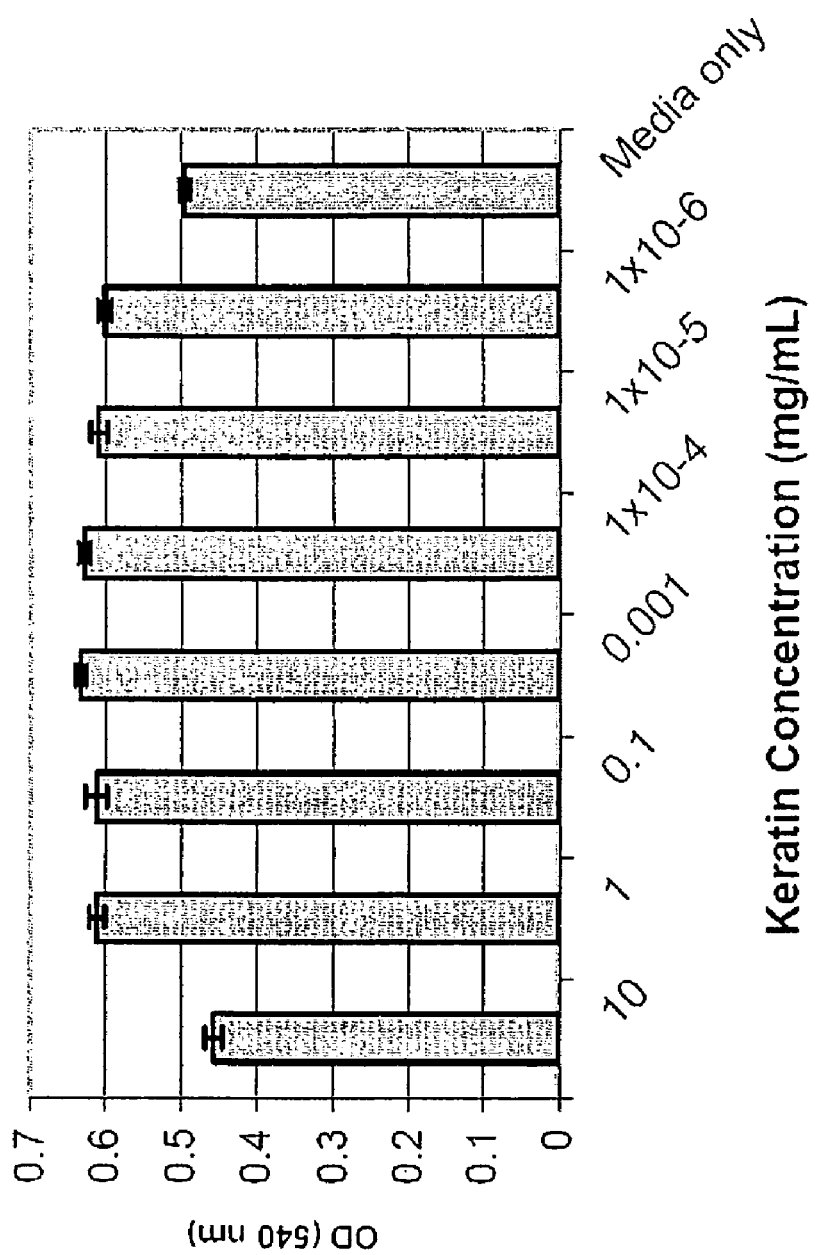
FIG. 3. Assessment of in vitro keratin biocompatibility on RT4-D6P2T Schwann cells by an MTS assay. Cells cultured in the presence of keratin dissolved in media showed significantly higher rates of proliferation at concentrations ranging from 0.1 µg/mL to 1 mg/mL of keratin in comparison to fetal bovine serum containing media alone.

Increasing the number of cells through enhanced proliferation improves regeneration in larger tissue injuries. The ability of keratin to induce cell multiplication was tested with RT4-D6P2T Schwann cells using the so-called MTS assay, a test that correlates metabolic reduction of a tetrazolium salt to cell number (Cory A. H. et al., Cancer Commun 1991; 3(7): 207-12). The cell line was shown to be similar to primary cultures of Schwann cells in previous studies (Hai M. et al., J Neurosci Res 2002; 69(4):497-508). Dilutions of keratin in basal media were added to cell cultures and incubated for 24 hours. The growth response of the cells was measured and compared to basal media containing fetal bovine serum (FIG. 3). The proliferation data shows a normal distribution of dose response with inhibition at the highest dose tested (10 mg/mL). This is not unexpected as normal hair follicle cycling is controlled by both stimulatory and inhibitory molecules. At higher doses of keratin, it is reasonable to assume that inhibitory factors may dominate. When the keratin concentrations were reduced, even as low as 1 ng/mL, results showed statistically significant increases in cell growth over media containing serum.

Figure 4:
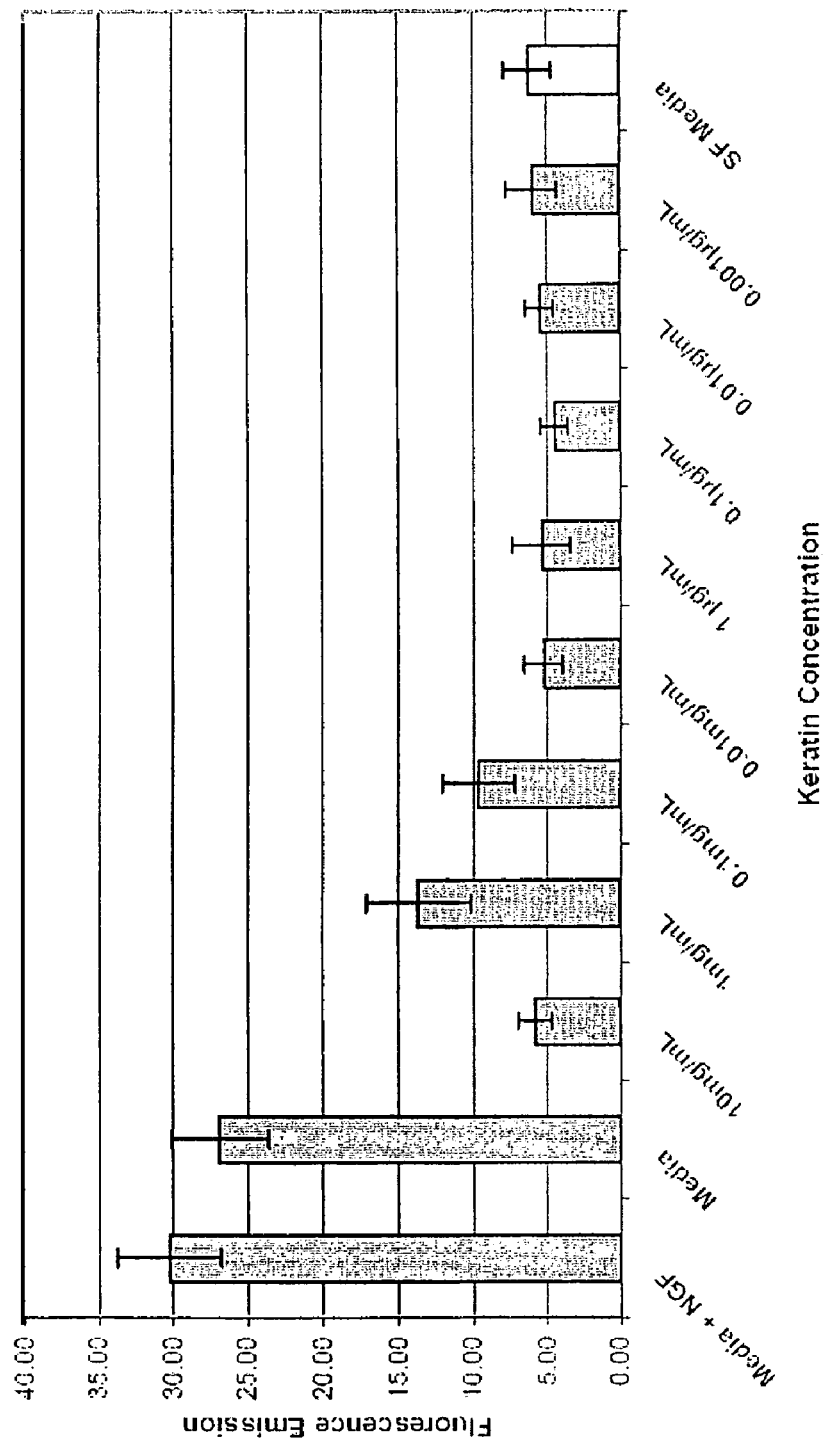
FIG. 4. In vitro migration of Schwann cells in response to keratin in a modified Boyden chamber. Keratin in serum-free media is chemotactic for Schwann cells at 1 mg/mL and 0.1 mg/mL concentrations.

The RT4-D6P2T Schwann cells were used to investigate this phenomenon in the presence of several dilutions of keratin in basal media. Media with serum and basal media without serum served as positive and negative controls, respectively. Media with serum plus nerve growth factor (NGF, 50 ng/mL), a known chemotactic agent for Schwann cells, was also included for comparison. Keratin was able to enhance Schwann cell migration at two of the higher concentrations tested, albeit not as markedly as in the positive controls (FIG. 4).

Figure 5:
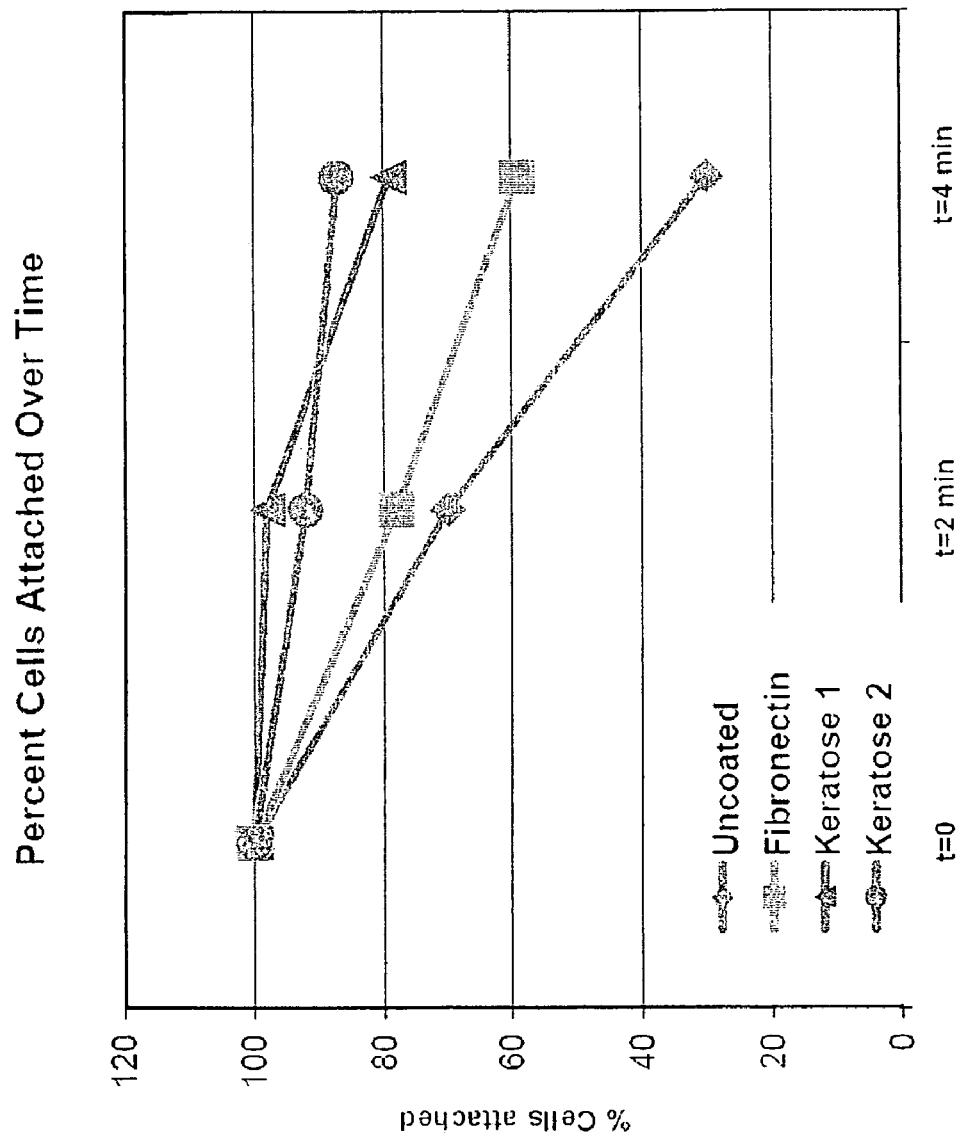
FIG. 5. Biomaterial coated plates seeded with Schwann cells were placed into the chamber system and exposed to a constant flow rate at 37 degrees Celsius under a microscope. Phase contrast images were captured at different time points and the percentage of cells that remained attached over time was quantified. After 4 minutes, it was found that 81.3% of the cells remained attached on the keratin biomaterial (keratose) in comparison to 59% on fibronectin and 30% on uncoated slides.

Keratin was coated onto glass microscope slides and RT4-D6P2T Schwann cells cultured on this substrate. After allowing time for attachment, the slides were placed into a specially designed flow chamber that exposed the cells to a high shear environment. Light microscopy was used to monitor the number of cells remaining attached under constant shear at increasing time intervals. The results indicated that the cells adhered more strongly to a keratin substrate than some other ECM molecules typically used to promote cell adhesion (FIG. 5). More than 80% of cells remained attached to the keratin substrate while less than 60% maintained adhesion to fibronectin, a common matrix molecule containing RGD binding domains.

Cells were plated at a density of 10,000 cells/well on a 48 well tissue culture plate (Corning Life Sciences, Lowell, Mass.). After 24 hours, the standard culture media was removed and the cells were serum-starved in FBS free media supplemented with 1% Penicillin/Streptomycin and 1% L-Glutamine for 24 hours. Cells were then exposed to solutions of keratin dissolved in media at concentrations ranging from 10 mg/mL to 100 ng/mL. Cultures were grown to 90% confluency, at which point cell viability was assessed using the MTS assay (Promega Corp., Madison, Wis.) according to the manufacturer's instructions. The absorbance was measured on a BioTek ELX-500 UV plate reader (BioTek Instruments, Inc., Winooski, Vt.).

A modified Boyden chamber (Chemicon® QCM™ Chemotaxis Assay, Chemicon/Millipore, Temecula, Calif.) was used to assess the chemotactic properties of keratin to rat RT4-D6P2T cells. Cells were passaged five times and cultured to 70% confluency. Cells were then serum-starved in FBS free media for 24 hours. Cells were trypsinized, resuspended in serum-free media to a concentration of 1.2×10$^6$ cells/mL and placed in a well with a semi-permeable (8 μm pore diameter) membrane separating the cells from the experimental solution. Two positive controls were used: a) standard RT4-D6P2T culture media, and b) standard media supplemented with 20 ng/mL of nerve growth factor (NGF). Serum-free DMEM served as the negative control. The keratin was dissolved in serum-free media at concentrations of 10 mg/mL, 1 mg/mL, 0.1 mg/mL, 0.01 mg/mL, 1 μg/mL and 0.1 μg/mL and sterile filtered (0.45 μm). Cells were incubated for 24 hours in the presence of control or keratin-containing solutions placed below the trans-wells (n=8 per group). Following detachment, the cells were lysed and fluorescently labeled according to the manufacturer's instructions. A fluorescence plate reader was used to obtain readings (FLx800, BioTek, Winooski, Vt.).

Schwann cell adhesion to keratin biomaterials was examined using a parallel flow chamber apparatus (Glycotech, Gaithersburg, Md.). Tissue culture treated 35 mm glass slides (Corning, Acton, Mass.) were coated with a biomaterial: keratin (experimental), fibronectin (positive control) or left uncoated (negative control). Schwann cells were seeded onto coated slides, placed into a vacuum flow chamber and subjected to flow-induced sheer stress. Phase contrast images were taken every 2 minutes using a Zeiss Axiovert 100 microscope (Carl Zeiss Microimaging, Inc., Thornwood, N.Y.) and the percentage of adherent cells was quantified over time using digital image analysis software (SigmaScan Pro 5.0, Systat, San Jose, Calif.).

The keratin molecules themselves likely provided specific sites of cell attachment as evidenced by the enhanced in vitro cell binding. Schwann cell proliferation was significantly increased across a broad range of keratin concentrations and migration was up-regulated at several concentrations.

Example 9

Gene Expression

To determine the potential effect keratin might have on transcriptional regulation of RT4-D6P2T Schwann cells, quantitative reverse transcription polymerase chain reaction (RT-PCR) was used to determine the levels of transcription of several important proteins. S10 is a calcium binding protein that is responsible for calcium homeostasis and normal glial cell function (Xiong Z et al., Exp Cell Res 2000; 257(2):281-9); L1 CAM is a neuro-glial cell adhesion molecule expressed in both myelinating and non-myelinating Schwann cells (Ide C, Neurosci Res 1996; 25(2):101-21; Fu S Y and Gordon T. Mol Neurobiol 1997; 14(1-2):67-116); CD104 is the beta 4 integrin subunit and is important for Schwann cell to axon interaction (Feltri M L et al., *Development* 1994; 120(5): 1287-301).

The ability of keratin to induce expression of Schwann cell specific genes was examined using Real Time PCR. Three genes were selected for investigation: S100β, L1-CAM and CD-104. RT4-D6P2T cells were cultured for 72 hours in: a) media only (Control), b) keratin dissolved in media, or c) media on keratin coated culture plates. Total RNA was extracted from cell cultures (n=2 per group) using RNeasy® spin columns (Qiagen, Hilden, Germany) according to the manufacturers instructions with DNase I treatment on the columns. Extracted RNA was quantified using RiboGreen (Molecular Probes, Eugene, Oreg.) and 500 ng was reverse-transcribed into cDNA using oligo(dT) primers and Super-Script II, as per manufacturer's recommendations (Invitrogen). The QuantiTect SYBR Green RT-PCR kit (Qiagen) was used according to the manufacturer's instructions with 50 ng total RNA per sample. Reactions were run on the ABI 7300 Real-time PCR System (Applied Biosystems, Foster City, Calif.) with appropriate controls. Relative expression of genes of interest was determined following normalization to the level of a housekeeping gene, Glyseraldehyde-3-phosphate dehydrogenase (GAPDH) in each sample.

Figure 6:
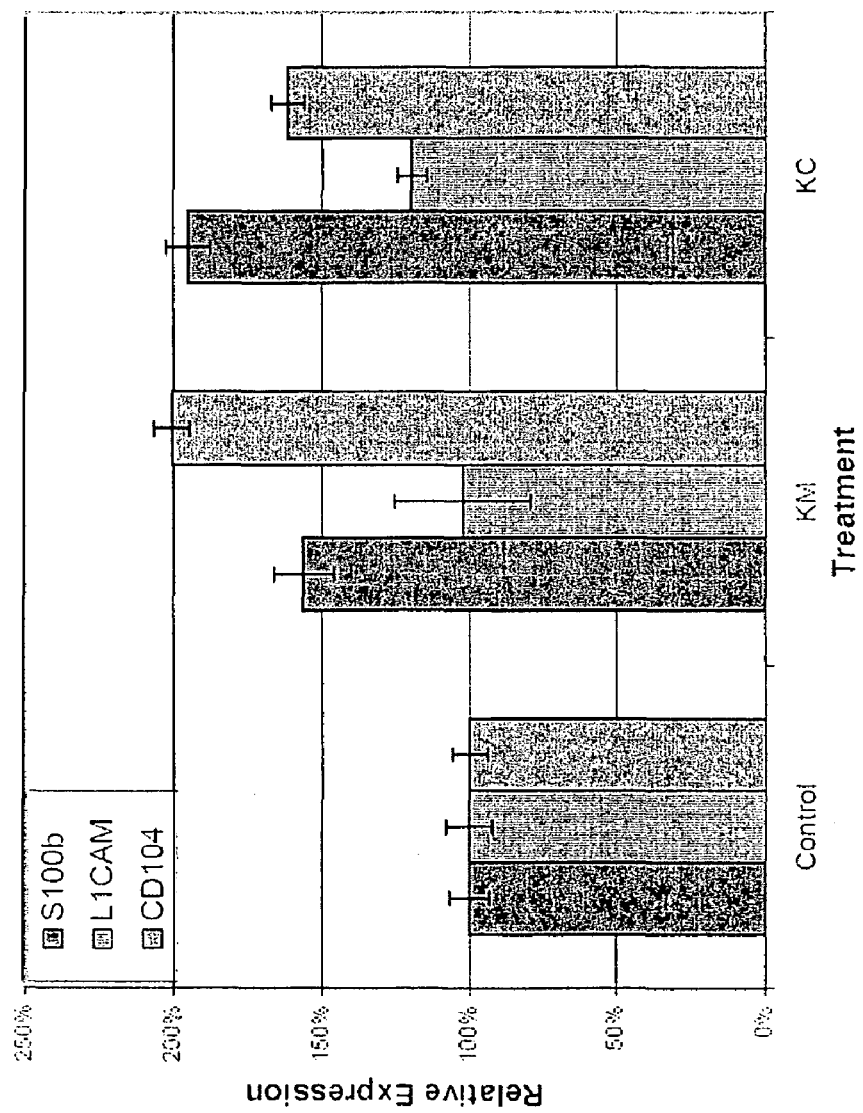
FIG. 6. RT4-D6P2T gene expression changes following 72 hours of culture in keratin containing media (KM), on keratin coated dishes (KC) or in standard culture conditions (Control). Expression of the myelinating protein S100β and integrin CD104 was significantly increased in both keratin-treated cultures. There was no significant change in L1-CAM expression.

The interaction of Schwann cells with keratin either as a substrate or soluble molecules—both likely scenarios in the gel state in vivo—resulted in increased expression of regulatory genes. Quantitative RT-PCR data showed up-regulation of S100, and CD104 when the keratin was exposed to the cells in either manner. L1CAM appeared to be unaffected. CD104 was up-regulated more than two-fold when keratin was added to the media, while S100β similarly increased when the cells were culture on a keratin substrate (FIG. 6).

Example 10

Animal Model and Surgical Procedures

Figure 7:
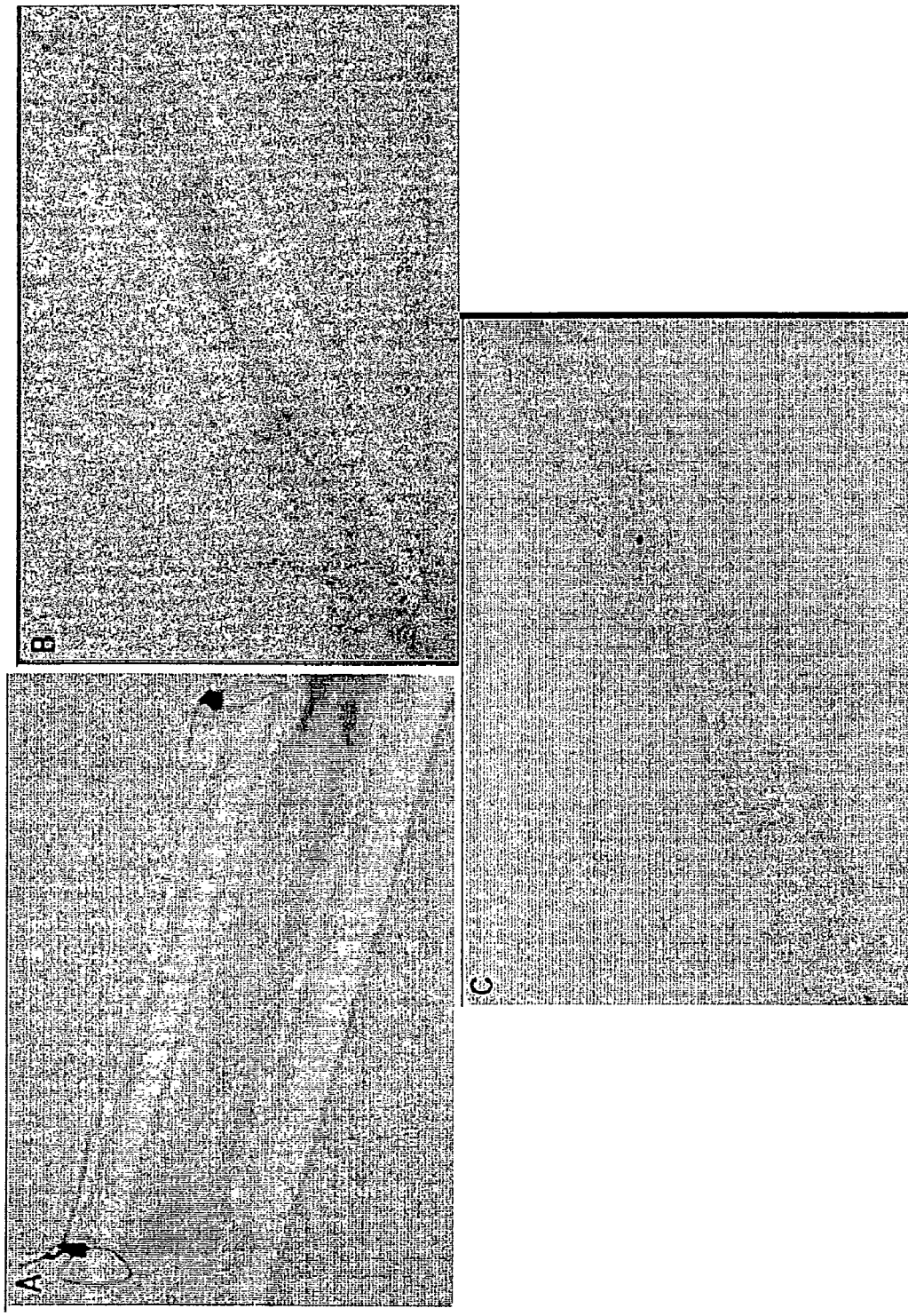
FIG. 7. Nerve fiber regeneration 6 weeks after repair in empty (A), keratin (B), and autograft (C) treated animals. In keratin and autograft groups, bridging of the nerve gap was observed in 100% of the animals, whereas only 50% of the animals in the empty group showed regeneration across the defect.

To directly test the effect of keratin biomaterial hydrogel on regeneration, a nerve injury model in mice was employed. The tibial nerve on one side of the mouse was transected and the proximal and distal ends of the nerve placed inside a silicone tube or conduit, creating a 4 mm gap. The nerve ends were sutured to the conduit and keratin gel injected into the gap space with a syringe and small needle. At 6 weeks, 100% of the animals in the keratin (5/5) and autograft (8/8) groups showed visible axon regeneration across the 4 mm nerve gap, whereas only 50% (5/10) of the animals in the empty conduit group displayed visible fiber regeneration (FIG. 7). Animals which did not display visible fiber regeneration did not undergo further testing (electrophysiology, muscle force generation, and histology).

Adult male Swiss Webster mice were anesthetized with isoflurane (1-1.5 vol %), shaved and cleansed with Betadine. Animals were randomized and placed into either the empty conduit (n=10), keratin (n=5), or autograft (n=8) group. All surgical procedures were performed using aseptic technique. A 1.5 cm incision was made on the dorsum of the left thigh and the sciatic nerve was identified by dissection through the fascial plane separating the vastus lateralis and biceps femoris muscles. The tibial nerve was separated from the common peroneal and sural nerves proximally, and from its insertion into the gastrocnemius muscle to the tendon of obturator externus. The tibial nerve was transected 5 mm proximal to its insertion into the gastrocnemius. For the conduit groups, the proximal and distal nerve ends were secured inside a 7 mm tube made of Silastic® medical grade elastomer (0.64±0.13 mm inside diameter, 1.19±0.13 mm outside diameter, 0.28 mm wall diameter, Dow Corning, Mich.) using 10-0 Nylon microsuture. The nerve gap within the conduit, defined as the distance between the proximal and distal nerve ends, was measured at 4.0 mm in all animals. For animals in the keratin group, following placement of the proximal and distal nerve ends a sterilized keratin gel was introduced into the 4 mm nerve gap using a 10 cc syringe and subcutaneous needle. The needle was passed into the nerve gap by placing it between the internal wall of the conduit and the nerve end. The needle was then advanced to the distal end of the gap, and the keratin hydrogel was ejected as the needle was withdrawn. In the autograft group, the sural nerve was identified through an incision made between the medial and lateral heads of the gastrocnemius. Approximately 14 mm of the sural nerve was harvested to allow for nerve retraction and trimming of the proximal and distal ends. A 4 mm threecable graft was made by looping the nerve back and forth upon itself. Proximal and distal epineurial sutures were placed to maintain cable positioning during fixation. The three proximal sural nerve cables were secured around the circumference of the proximal tibial nerve end 120° apart using 11-0 microsuture. This process was repeated distally. A deep muscle closure was performed around the conduit using 8-0 Nylon microsuture, followed by superficial muscle and skin closure with 5-0 Vicryl® suture. The wound was then coated with Neosporin® triple antibacterial ointment.

Example 11

Functional Testing (Electrophysiology and Muscle Force Generation)

At 6 weeks following nerve injury and repair, each animal underwent functional testing of the tibial nerve. Following exposure of the tibial nerve, a Nicolet Viking IIe electrodiagnostic system (Nicolet Instrument Corp. Madison, Wis.) was used to test nerve latency and action potential amplitude. A bipolar stimulating electrode was placed on the tibial nerve at the level of the obturator externus tendon. The active recording electrode was placed on the gastrocnemius muscle belly with the reference recording electrode placed on the foot. The nerve was then stimulated with a constant current stimulus at a level of 1.0 milli-Amps for a duration of 0.1 milliseconds. The testing protocol was repeated three times and the average value recorded. For muscle force measurements each limb was immobilized using K-wires driven through the femur and the tibia to fix the leg to a wooden table, preventing motion of the limb during testing. The gastrocnemius remained in situ until the force generation studies were started. The plantaris and soleus tendons were transected, leaving the Achilles tendon/gastrocnemius complex isolated. A wire suture was tied around the distal end of the Achilles tendon. The tendon was then transected distal to the suture, and the suture was attached to a force transducer (Model FT03, Grass Instrument Co., Quincy, Mass.) connected to a force transducer amplifier (Model 13-G4615-50, Gould Inc., Cleveland, Ohio). The tibial nerve was then directly stimulated 4 mm proximal to the conduit (SD9 stimulator, Grass Instrument Co.) with increasing voltage until the maximum isometric single twitch force was obtained. The frequency of stimulation was then increased until maximum tetanic contractile force was generated. The same procedure was repeated on the contralateral limb which served as the control. Responses were recorded using a calibrated recording oscillograph (RS 3800, Gould Inc.) connected to the force transducer.

The data demonstrate that keratin gel-filled conduits facilitated significantly improved nerve conduction and signal amplitude, even when compared to autograft. Muscle function recovery, a challenging outcome at a six-week time point, was statistically indistinguishable between the keratin and autograft groups.

Figure 8A:
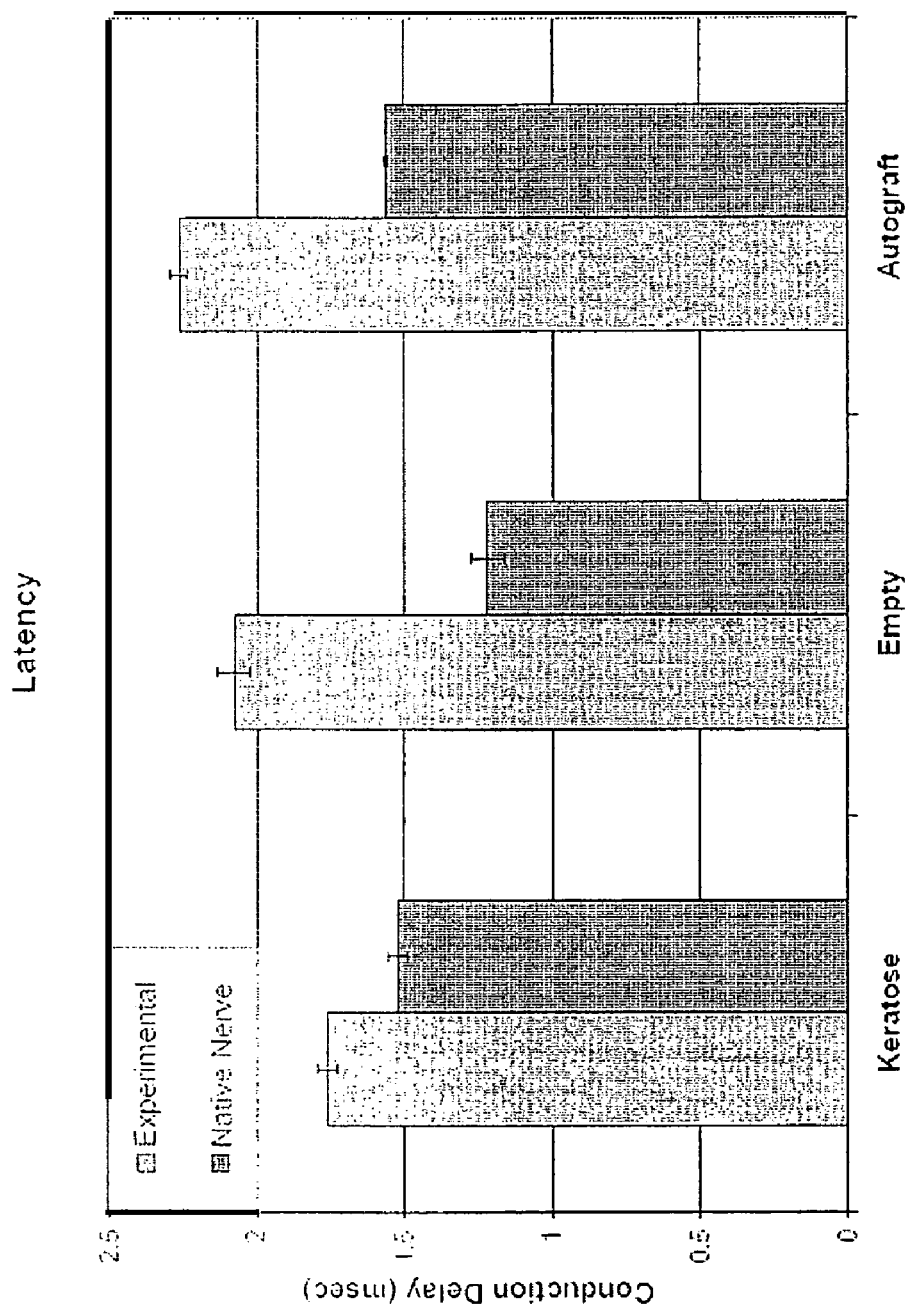
FIGS. 8A-8B. Electrophysiology testing following 6 weeks of regeneration showed an improvement in conduction delay (FIG. 8A) and amplitude of the nerve impulse (FIG. 8B) in keratin-filled tubes versus empty and autograft.

The latency (conduction delay) and amplitude of the motor action potential were averaged for each treatment group and compared to its contralateral control. After 6 weeks of regeneration, latency measurements revealed that the conduction delay was significantly ($p<0.05$) better in keratin (1.76 msec) than either the empty conduit (2.10 msec) or autograft (2.26 msec) groups (FIG. 8A).

Figure 8B:
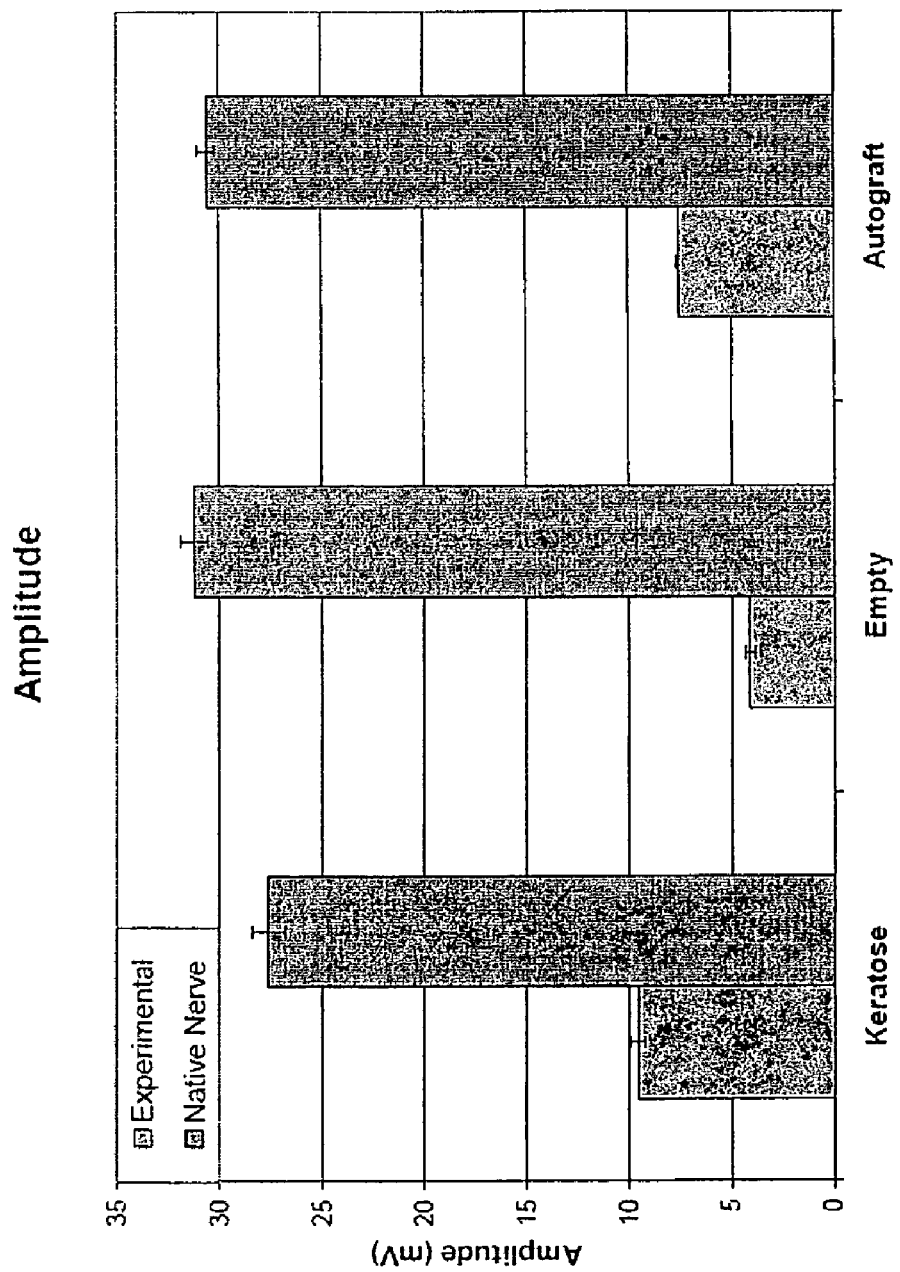

These data also show that the keratin treated nerves were not significantly different than their contralateral control ($p>0.05$), while conduction delay was significantly increased over the contralateral control in both the empty conduit and autograft groups ($p>0.05$ in both cases). The difference in recovery of amplitude of the motor action potential was also statistically less ($p<0.05$) in the keratin group (27.61 mV) than both the empty conduit (31.23 mV) and autograft (30.59 mV) groups. However, all groups displayed significantly less signal amplitude that their contralateral controls (FIG. 8B). This is to be expected at such an early time point as muscle function recovery lags behind nerve recovery.

Figure 9A:
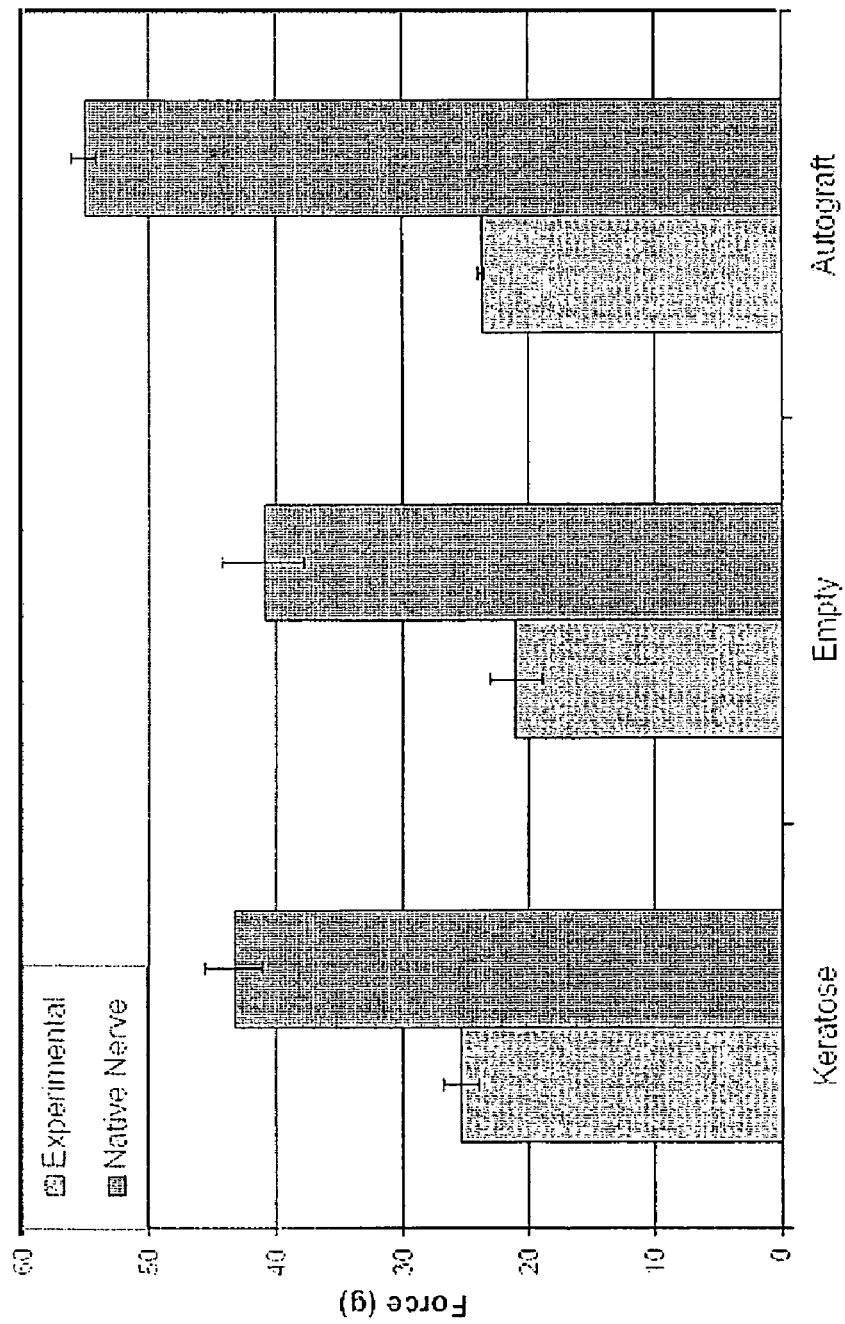
FIGS. 9A-9B. Muscle force testing at 6 weeks following regeneration showed a return of muscle single twitch (FIG. 9A) and muscle tetanus (FIG. 9B) in all treatment groups.
Figure 9B:
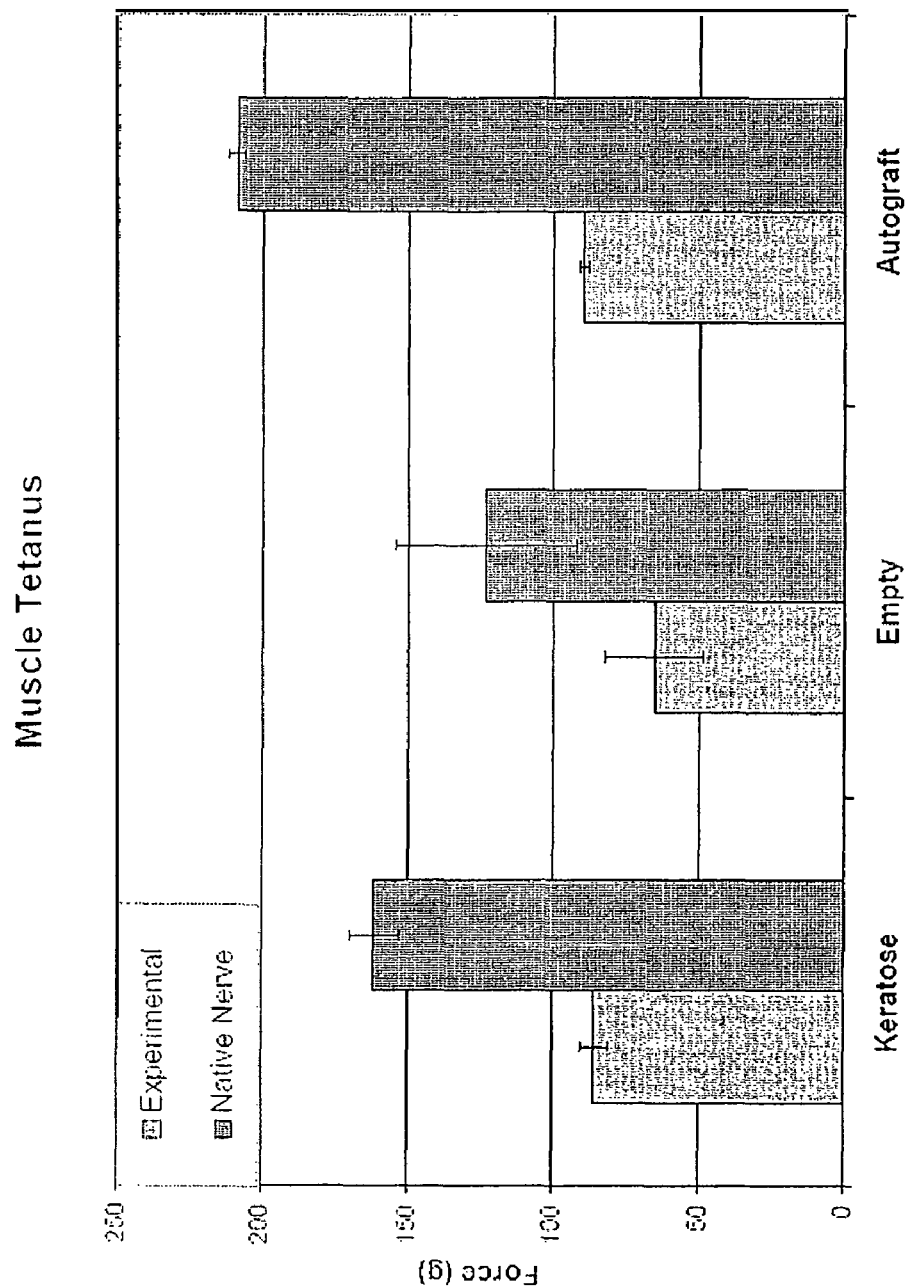

Maximum single twitch and maximum tetanus were measured in grams and averaged for each experimental and control group. After 6 weeks, the recovery of maximum single twitch force was 25.3 g in the keratin group, 21.0 g in the empty conduit group, and 23.8 g in the autograft group (FIG. 9A). Recovery of maximum tetanus was 85.3 g in the keratin group, 65.0 g in the empty conduit group, and 89.0 g in the autograft group (FIG. 9B). These data were not statistically significant ($p>0.05$) between groups, but were significantly ($p>0.05$) lower than their contralateral controls.

Example 12

Nerve Harvest and Histology

Following testing of the gastrocnemius muscle, the tibial nerve was transected 4 mm proximal and 4 mm distal to the nerve conduit. This nerve segment was then pinned to hardened silicone to prevent shrinkage. The nerves were covered in 4% paraformaldehyde for 24-48 hours, washed with a 0.15 mol/L phosphate buffer solution overnight and postfixed in 1% osmium tetroxide. The nerve segments were then placed in a phosphate buffered saline, dehydrated in increasing concentrations of ethanol (50% to 100) and embedded using epoxy resin (Polysciences, Inc., Warrington, Pa.). Semi-thin sections (1 μm) were cut from each pre-trimmed block of tissue using an LKB III Ultramicrotome (LKB-Produkter A.B., Broma, Sweden), stained with 1% toluidine blue and mounted on slides for analysis by light microscopy. Nerves were qualitatively assessed for the preservation of nerve architecture, quality and quantity of regenerated nerve fibers and extent of myelination. Nerve fiber area and degree of vascularization was digitally quantified for each treatment group using SigmaScan Pro 5.0. Ultra-thin sections (85 nm) were cut with an ultramicrotome (Leica Microsystems, Bannockburn, Ill.), placed on 200-mesh copper grids, stained with 1% uranyl acetate in 25% methanol for 7 min, rinsed, stained with Venable's lead citrate for 7 min, dried, and examined on a transmission electron microscope (TEM, Model 515, Philips/FEI Co., Hillsboro, Oreg.).

Graphical data are presented as means plus or minus standard error. Single-factor analysis of variance (ANOVA) was used to determine differences between treatment groups in the in vitro assays and significance differences established at $p<0.05$ with Tukey's method using the Studentized range statistic. A two-tailed, unpaired, two-sample Student's t-test with unequal variance was used to determine differences between test groups in the in vivo regeneration experiments. A p value less than 0.05 was considered significant.

The histomorphometric analysis revealed that nerves regenerated through a keratin hydrogel were larger in diameter and had more supportive vasculature than did the autografts.

Figure 10:
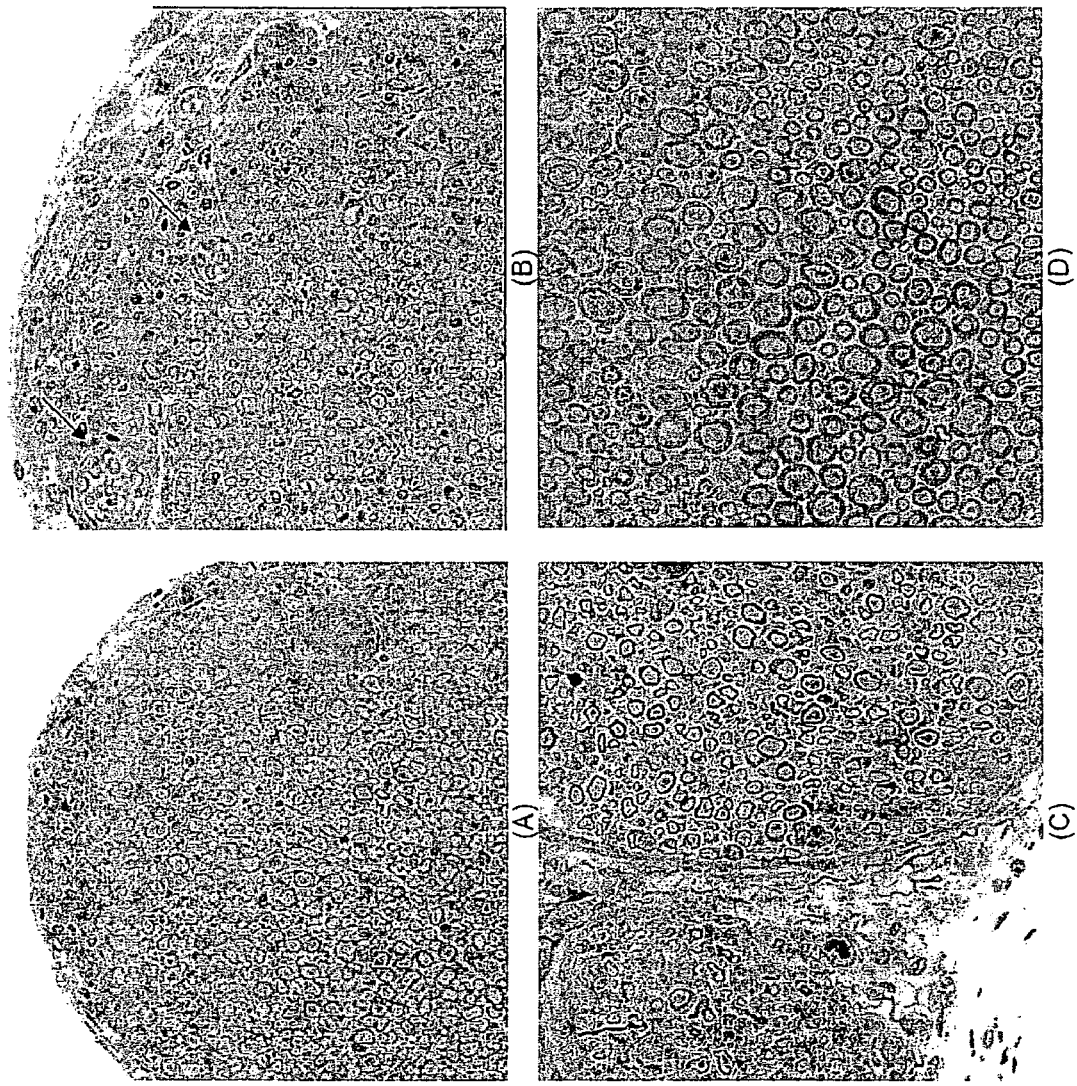
FIG. 10. Toluidine blue staining of regenerated nerve cross-sections showing myelinated axons in all groups: empty (A), keratin (B), autograft (C), and native nerve (D). Increased vascularization (arrows) was observed in the keratin group in comparison to all treatment groups and native nerve control.
Figure 11A:
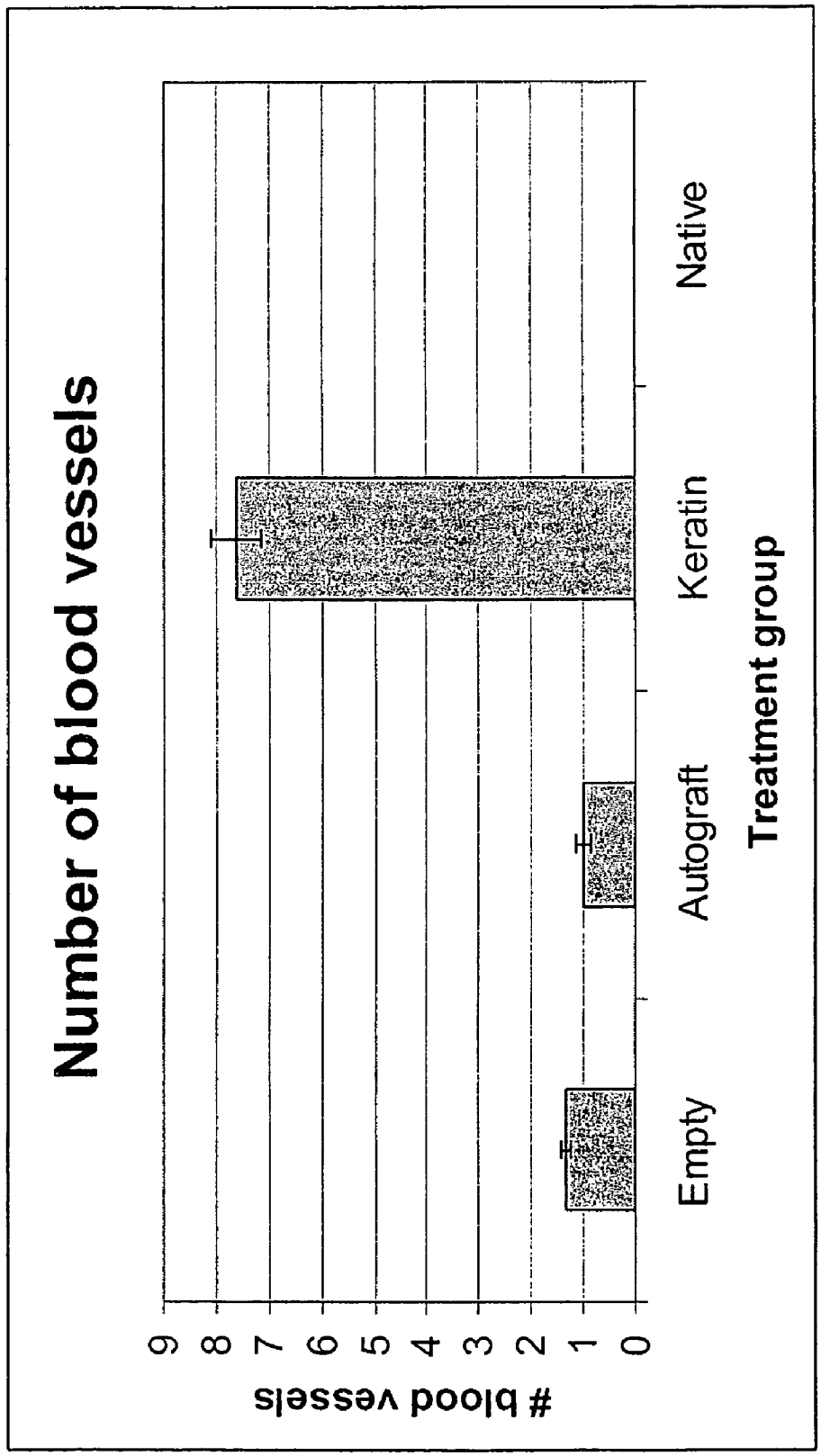
FIGS. 11A-11B. Histomorphometric analysis of regenerated nerve cross sections. Overall nerve area was greatest in the keratin treated group (FIG. 11A). The robust angiogenic response noted upon gross observation was confirmed by the larger number of blood vessels present in the keratin-treated nerves (FIG. 11B). (n=5, 5, 8, and 5, respectively, for empty, keratin, autograph, and native nerve groups.)
Figure 11B:
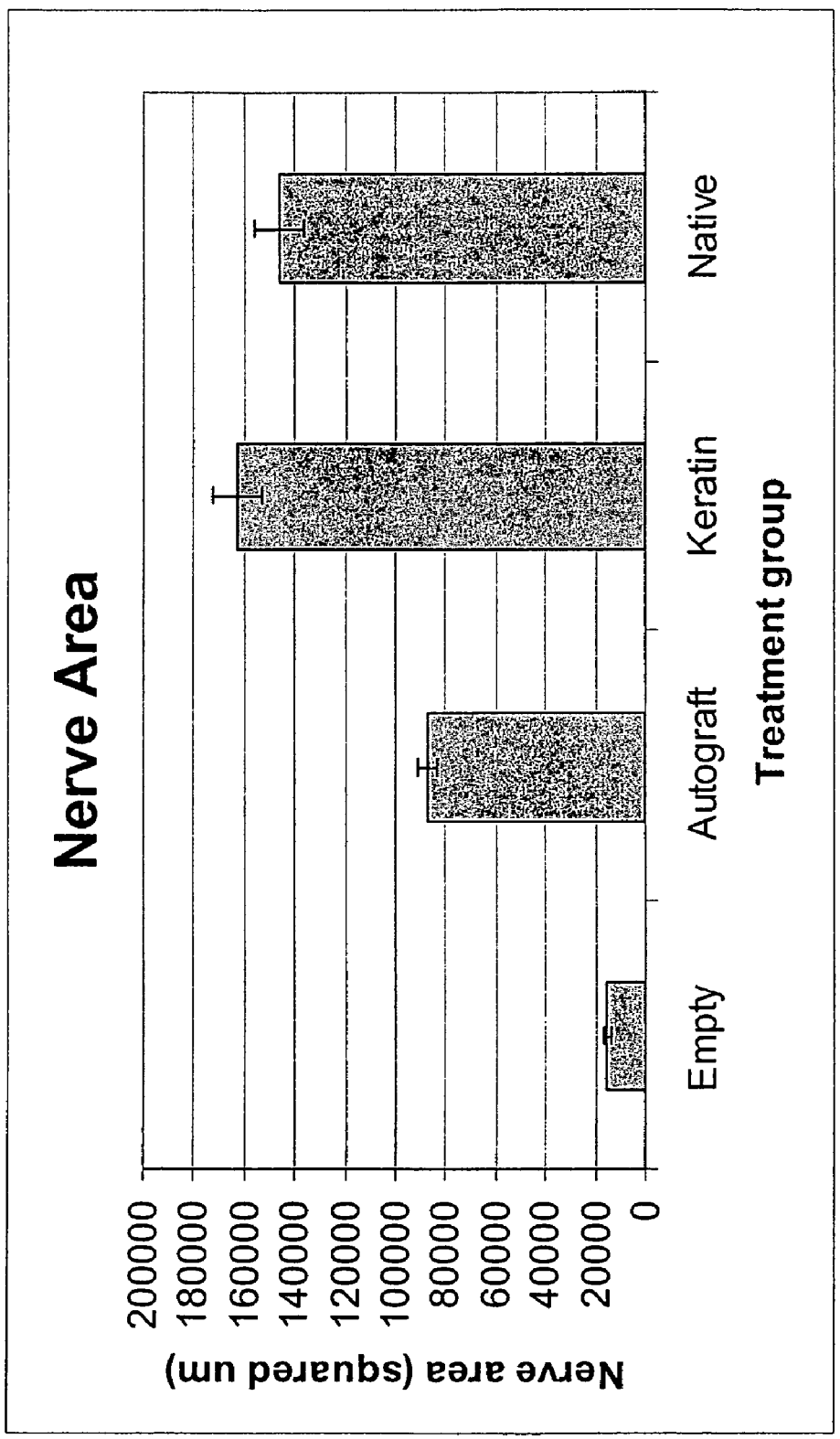

There was no apparent difference in myelination at 6 weeks between treatment groups (FIG. 10). However, histomorphometric analysis of cross-sections demonstrated a statistically significant ($p<0.05$) increase in the overall nerve area (FIG. 11A) in the keratin group compared to the empty conduit and autograft groups. Interestingly, nerves treated with keratin-filled conduits were significantly more vascularized in comparison to both empty conduits and autograft. Nerve fibers that regenerated through keratin-filled conduits had a significantly ($p<0.05$) larger number of blood vessels in comparison to all other groups (FIG. 11B).

The foregoing is illustrative of the present invention, and is not to be construed as limiting thereof. The invention is defined by the following claims, with equivalents of the claims to be included therein.

That which is claimed is:

1. A method for promoting the growth of a peripheral nerve in a mammal, comprising:
   encasing a damaged region of said nerve in a support structure having an elongate opening therein; and
   administering a physiologically acceptable matrix composition into said opening, said matrix composition comprising a soluble keratose, kerateine, or a mixture thereof, in an amount effective to promote the growth of said nerve at said damaged region.

2. The method of claim 1, wherein said damaged region of said nerve is a crushed region.

3. The method of claim 1, wherein said damaged region of said nerve is a severed region having proximal and distal stumps, and said encasing step is carried out by placing the proximal and distal stumps of said nerve in said support structure.

4. The method of claim 1, wherein said nerve is a peripheral nerve selected from the group consisting of sensory-somatic nerves and autonomic nerves.

5. The method of claim 1, wherein said matrix composition comprises a soluble alpha keratose.

6. The method of claim 1, wherein said matrix composition comprises a soluble acidic alpha keratose.

7. The method of claim 1, wherein said matrix composition further comprises a nerve growth factor.

8. The method of claim 7, wherein said nerve growth factor is provided in a concentration of 1-100 ng/mL of said matrix composition.

9. The method of claim 1, wherein said support structure is formed from a bioabsorbable material.

10. The method of claim 1, wherein said support structure is formed from an inert polymeric material.

11. The method of claim 1, wherein said support structure further comprises one or more electrodes operatively associated with said support structure.

12. The method of claim 1, wherein said soluble keratose, kerateine, or mixture thereof is provided in a concentration from 0.01 mg/mL to 10 mg/mL.

13. The method of claim 1, wherein said matrix composition consists essentially of a soluble keratose, kerateine, or a mixture thereof.

14. The method of claim 1, wherein said matrix composition comprises a soluble alpha keratose, gamma keratose, or a mixture thereof.

15. The method of claim 1, wherein said support structure comprises collagen.

16. The method of claim 1, wherein said matrix composition comprises a soluble acidic keratose, kerateine, or a mixture thereof.

17. The method of claim 1, wherein said matrix composition comprises a hydrogel of said keratose, kerateine, or mixture thereof.

18. A method for promoting the growth of a peripheral nerve in a mammal, comprising:
   encasing a damaged region of said nerve in a support structure having an elongate opening therein; and
   administering a physiologically acceptable matrix composition into said opening, said matrix composition consisting essentially of a soluble acidic keratose, kerateine, or a mixture thereof, in an amount effective to promote the growth of said nerve at said damaged region.

19. The method of claim 18, wherein said matrix composition comprises a soluble acidic alpha keratose, acidic gamma keratose, or a mixture thereof.

20. The method of claim 18, wherein said matrix composition comprises a soluble acidic alpha keratose.

21. The method of claim 18, wherein said soluble acidic keratose, kerateine, or mixture thereof is provided in a concentration from 0.01 mg/mL to 10 mg/mL.

22. The method of claim 18, wherein said support structure is formed from an inert polymeric material.

23. The method of claim 18, wherein said support structure is formed from a bioabsorbable material.

24. The method of claim 18, wherein said support structure comprises collagen.

25. The method of claim 18, wherein said matrix composition further comprises a nerve growth factor.

26. The method of claim 25, wherein said nerve growth factor is provided in a concentration of 1-100 ng/mL of said matrix composition.

27. The method of claim 18, wherein said support structure further comprises one or more electrodes operatively associated with said support structure.

28. The method of claim 18, wherein said acidic keratose, acidic kerateine, or mixtures thereof is provided in a concentration from 0.01 mg/mL to 10 mg/mL.

29. The method of claim 18, wherein said matrix composition comprises a hydrogel of said keratose, kerateine, or mixture thereof.

* * * * *